United States Patent
Shimamura et al.

(10) Patent No.: US 11,819,537 B2
(45) Date of Patent: *Nov. 21, 2023

(54) PREVENTIVE OR THERAPEUTIC METHOD FOR INFLAMMATORY SKIN DISEASE

(71) Applicant: Osaka University, Osaka (JP)

(72) Inventors: Munehisa Shimamura, Osaka (JP); Hironori Nakagami, Osaka (JP); Yuka Ikeda, Osaka (JP); Ryuichi Morishita, Osaka (JP); Hiroshi Koriyama, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 1182 days.

This patent is subject to a terminal disclaimer.

(21) Appl. No.: 16/345,028

(22) PCT Filed: Nov. 7, 2017

(86) PCT No.: PCT/JP2017/040115
§ 371 (c)(1),
(2) Date: Jul. 15, 2019

(87) PCT Pub. No.: WO2018/084311
PCT Pub. Date: May 11, 2018

(65) Prior Publication Data
US 2019/0365859 A1 Dec. 5, 2019

(30) Foreign Application Priority Data

Nov. 7, 2016 (JP) .................................. 2016-216958

(51) Int. Cl.
| | | |
|---|---|---|
| *A61P 29/00* | (2006.01) | |
| *A61K 38/19* | (2006.01) | |
| *A61P 17/06* | (2006.01) | |
| *A61K 9/06* | (2006.01) | |
| *A61K 38/08* | (2019.01) | |
| *A61P 17/00* | (2006.01) | |

(52) U.S. Cl.
CPC .............. *A61K 38/191* (2013.01); *A61K 9/06* (2013.01); *A61K 38/08* (2013.01); *A61P 17/00* (2018.01); *A61P 17/06* (2018.01)

(58) Field of Classification Search
None
See application file for complete search history.

(56) References Cited

U.S. PATENT DOCUMENTS 10,517,926 B2 * 12/2019 Shimamura ............. A61P 29/00
2018/0147259 A1   5/2018 Shimamura et al.

FOREIGN PATENT DOCUMENTS

| | | |
|---|---|---|
| JP | 2005/514919 A | 5/2005 |
| JP | 2009/536171 A | 10/2009 |
| KR | 2003/0003639 | 1/2003 |
| WO | WO-03/033664 A2 | 4/2003 |
| WO | WO-2007/128564 A2 | 11/2007 |
| WO | WO-2014/119438 A1 | 8/2014 |
| WO | WO-2016/186071 A1 | 11/2016 |

OTHER PUBLICATIONS

Bhattacharya, R., et al. PLOS ONE; 12(3):1-22 (Year: 2017).*
Cheng et al "Disabling of Receptor Activator of Nuclear Factor-kB (RANK) Receptor Complex by Novel Osteoprotegerin—Like Peptidomimetics Restores Bone Loss In Vivo" The Journal of Biological Chemistry vol. 279, pp. 8269-8277, 2004.
Cheng et al "Mutations Within the TNF-Like Core Domain of RANKL Impair Osteoclast Differentiation and Activation" Molecular Endocrinology vol. 23, pp. 35-46, 2009.
Kurinami et al "A Novel Therapeutic Peptide as a Partial Agonist of RANKL in Ischemic Stroke" Scientific Reports vol. 6, pp. 1-11, 2016.
Lam et al "Crystal Structure of the TRANCE/RANKL Cytokine Reveals Determinants of Receptor-Ligand Specificity" The Journal of Clinical Investigation vol. 108, pp. 971-979, 2001.
Shimamura et al "OPG/RANKL/RANK Axis is a Critical Inflammatory Signaling System in Ischemic Brain in Mice" PNAS vol. 111, pp. 8191-8196, 2014.
Leibbrandt et al: "Novel Functions of RANK(L) Signaling in the Immune System", Retinal Degenerative Diseases: Advances in Experimental Medicine and Biology, Jun. 8, 2010, vol. 658, pp. 77-94.
La Manna et al: "Peptides as Therapeutic Agents for Inflammatory-Related Diseases", International Journal of Molecular Sciences, Sep. 11, 2018, vol. 19, No. 9, 2714, pp. 1-18.

* cited by examiner

*Primary Examiner* — G. R. Ewoldt
(74) *Attorney, Agent, or Firm* — Cesari & McKenna, LLP

(57) ABSTRACT

The present invention provides a preventive or therapeutic method for an inflammatory skin disease, such as psoriasis, the method comprising administering an oligopeptide as an active ingredient. More specifically, the invention provides a preventive or therapeutic method for an inflammatory skin disease, the method comprising administering an oligopeptide consisting of an amino acid sequence containing a DE loop sequence of RANKL protein and a β-strand D sequence of RANKL protein placed adjacent to the N-terminal side of the DE loop sequence.

9 Claims, 19 Drawing Sheets
Specification includes a Sequence Listing.

a)

b)

c)

SEQUENCE LISTING

<160> NUMBER OF SEQ ID NOS: 20

<210> SEQ ID NO 1
<211> LENGTH: 7
<212> TYPE: PRT
<213> ORGANISM: Homo sapiens

```
<400> SEQUENCE: 1

Ser Ile Lys Ile Pro Ser Ser
1               5

<210> SEQ ID NO 2
<211> LENGTH: 8
<212> TYPE: PRT
<213> ORGANISM: Mus musculus

<400> SEQUENCE: 2

Leu Met Val Tyr Val Val Lys Thr
1               5

<210> SEQ ID NO 3
<211> LENGTH: 11
<212> TYPE: PRT
<213> ORGANISM: Mus musculus

<400> SEQUENCE: 3

Tyr Leu Gln Leu Met Val Tyr Val Val Lys Thr
1               5                   10

<210> SEQ ID NO 4
<211> LENGTH: 8
<212> TYPE: PRT
<213> ORGANISM: Homo sapiens

<400> SEQUENCE: 4

Leu Met Val Tyr Val Thr Lys Thr
1               5

<210> SEQ ID NO 5
<211> LENGTH: 11
<212> TYPE: PRT
<213> ORGANISM: Homo sapiens

<400> SEQUENCE: 5

Tyr Leu Gln Leu Met Val Tyr Val Thr Lys Thr
1               5                   10

<210> SEQ ID NO 6
<211> LENGTH: 9
<212> TYPE: PRT
<213> ORGANISM: Mus musculus

<400> SEQUENCE: 6

His Asn Leu Met Lys Gly Gly Ser Thr
1               5

<210> SEQ ID NO 7
<211> LENGTH: 7
<212> TYPE: PRT
<213> ORGANISM: Mus musculus

<400> SEQUENCE: 7

His Asn Leu Met Lys Gly Gly
1               5

<210> SEQ ID NO 8
<211> LENGTH: 9
<212> TYPE: PRT
<213> ORGANISM: Homo sapiens

<400> SEQUENCE: 8
```

His Thr Leu Met Lys Gly Gly Ser Thr
1               5

<210> SEQ ID NO 9
<211> LENGTH: 7
<212> TYPE: PRT
<213> ORGANISM: Homo sapiens

<400> SEQUENCE: 9

His Thr Leu Met Lys Gly Gly
1               5

<210> SEQ ID NO 10
<211> LENGTH: 10
<212> TYPE: PRT
<213> ORGANISM: Mus musculus

<400> SEQUENCE: 10

His Glu Thr Ser Gly Ser Val Pro Ala Asp
1               5                   10

<210> SEQ ID NO 11
<211> LENGTH: 10
<212> TYPE: PRT
<213> ORGANISM: Homo sapiens

<400> SEQUENCE: 11

His Glu Thr Ser Gly Asp Leu Ala Thr Glu
1               5                   10

<210> SEQ ID NO 12
<211> LENGTH: 30
<212> TYPE: PRT
<213> ORGANISM: Mus musculus

<400> SEQUENCE: 12

Leu Met Val Tyr Val Val Lys Thr Ser Ile Lys Ile Pro Ser Ser His
1               5                   10                  15

Asn Leu Met Lys Gly Gly Ser Thr Lys Asn Trp Ser Gly Asn
            20                  25                  30

<210> SEQ ID NO 13
<211> LENGTH: 30
<212> TYPE: PRT
<213> ORGANISM: Mus musculus

<400> SEQUENCE: 13

Asp Tyr Leu Gln Leu Met Val Tyr Val Val Lys Thr Ser Ile Lys Ile
1               5                   10                  15

Pro Ser Ser His Asn Leu Met Lys Gly Gly Ser Thr Lys Asn
            20                  25                  30

<210> SEQ ID NO 14
<211> LENGTH: 28
<212> TYPE: PRT
<213> ORGANISM: Mus musculus

<400> SEQUENCE: 14

His Glu Thr Ser Gly Ser Val Pro Ala Asp Tyr Leu Gln Leu Met Val
1               5                   10                  15

Tyr Val Val Lys Thr Ser Ile Lys Ile Pro Ser Ser
            20                  25

```
<210> SEQ ID NO 15
<211> LENGTH: 15
<212> TYPE: PRT
<213> ORGANISM: Mus musculus

<400> SEQUENCE: 15

Leu Met Val Tyr Val Val Lys Thr Ser Ile Lys Ile Pro Ser Ser
1               5                   10                  15

<210> SEQ ID NO 16
<211> LENGTH: 15
<212> TYPE: PRT
<213> ORGANISM: Homo sapiens

<400> SEQUENCE: 16

Leu Met Val Tyr Val Thr Lys Thr Ser Ile Lys Ile Pro Ser Ser
1               5                   10                  15

<210> SEQ ID NO 17
<211> LENGTH: 22
<212> TYPE: PRT
<213> ORGANISM: Mus musculus

<400> SEQUENCE: 17

Leu Met Val Tyr Val Val Lys Thr Ser Ile Lys Ile Pro Ser Ser His
1               5                   10                  15

Asn Leu Met Lys Gly Gly
            20

<210> SEQ ID NO 18
<211> LENGTH: 30
<212> TYPE: PRT
<213> ORGANISM: Homo sapiens

<400> SEQUENCE: 18

Leu Met Val Tyr Val Thr Lys Thr Ser Ile Lys Ile Pro Ser Ser His
1               5                   10                  15

Thr Leu Met Lys Gly Gly Ser Thr Lys Tyr Trp Ser Gly Asn
            20                  25                  30

<210> SEQ ID NO 19
<211> LENGTH: 23
<212> TYPE: PRT
<213> ORGANISM: Mus musculus

<400> SEQUENCE: 19

Leu Met Val Tyr Val Val Lys Thr Ser Ile Lys Ile Pro Ser Ser His
1               5                   10                  15

Asn Leu Met Lys Gly Gly Ser
            20

<210> SEQ ID NO 20
<211> LENGTH: 26
<212> TYPE: PRT
<213> ORGANISM: Mus musculus

<400> SEQUENCE: 20

Leu Met Val Tyr Val Val Lys Thr Ser Ile Lys Ile Pro Ser Ser His
1               5                   10                  15

Asn Leu Met Lys Gly Gly Ser Thr Lys Asn
            20                  25
```

PREVENTIVE OR THERAPEUTIC METHOD FOR INFLAMMATORY SKIN DISEASE

CROSS-REFERENCE TO RELATED APPLICATIONS

This application is the National Stage of International Application No. PCT/JP2017/040115, filed Nov. 7, 2017, which claims the benefit of Japanese Application No. 2016-216,958, filed Nov. 7, 2016. The contents of both applications are hereby incorporated by reference in their entirety.

TECHNICAL FIELD

The present invention relates to a preventive or therapeutic agent etc. for an inflammatory skin disease.

BACKGROUND ART

Psoriasis is an inflammatory skin disease, typically accompanied by red rash, scaling, etc. The onset of psoriasis is said to involve, for example, abnormalities in T cells and keratinocytes, activation of a Toll-like receptor (TLR) 7 pathway and TLR8 pathway, and secretions of various inflammatory cytokines (e.g., TNF-α, IL-6, and IL-12/23p40) caused by the activation.

As for drugs for the treatment of psoriasis, infliximab and adalimumab are known as TNF-α inhibitors that regulate the expression of inflammatory cytokines, and ustekinumab is known as a human anti-IL-12/23p40 monoclonal antibody drug. However, a fundamental treatment for psoriasis has not yet been developed.

The number of patients with psoriasis has been increasing in recent years, and the market size of therapeutic drugs for psoriasis has also currently been expanding.

The inventors of the present invention have reported that RANKL protein inhibits inflammatory cytokines (Patent Literature (PTL) 1). However, PTL 1 only reports inflammatory cytokine inhibition via TLR2 and TLR4 pathways.

PTL 2 discloses that RANKL protein can be effective for contact allergic dermatitis. Although the full length of RANKL protein is used as an active ingredient in PTL 2, it is desirable to use a shorter oligopeptide as an active ingredient from the viewpoint of stability, economy, etc.

CITATION LIST

Patent Literature

PTL 1: WO 2014/051202
PTL 2: JP2009-536171A

Non-Patent Literature

NPL 1: The Journal of Clinical Investigation, No. 7, Vol. 108, 2001, pages 971-979
NPL 2: Mol Endocrinol, January 2009, 23(1): 35-46

SUMMARY OF INVENTION

An object of the present invention is to provide a preventive or therapeutic agent for an inflammatory skin disease, such as psoriasis, the agent comprising an oligopeptide as an active ingredient.

Technical Problem

As a result of extensive research to achieve the above object, the present inventors found, surprisingly, that an oligopeptide consisting of an amino acid sequence containing a DE loop sequence of RANKL protein and a β-strand D sequence of RANKL protein placed adjacent to the N-terminal side of the DE loop sequence has preventive and therapeutic effects on inflammatory skin diseases, such as psoriasis. Further research was conducted based on this finding. Consequently, the present invention has been completed.

Specifically, the present invention includes the following embodiments:

Item 1. A preventive or therapeutic agent for an inflammatory skin disease, the agent comprising an oligopeptide consisting of an amino acid sequence containing a DE loop sequence of RANKL protein and a β-strand D sequence of RANKL protein placed adjacent to the N-terminal side of the DE loop sequence,
wherein the DE loop sequence is the following amino acid sequence (a) or (b):
  (a) the amino acid sequence represented by SEQ ID NO: 1, or
  (b) an amino acid sequence with substitution, deletion, addition, or insertion of one amino acid in the amino acid sequence represented by SEQ ID NO: 1.

Item 2. The preventive or therapeutic agent according to Item 1, wherein the β-strand D sequence is the following amino acid sequence (c) or (d):
  (c) the amino acid sequence represented by any one of SEQ ID NOs: 2 to 5, or
  (d) an amino acid sequence with substitution, deletion, addition, or insertion of one to three amino acids in the amino acid sequence represented by any one of SEQ ID NOs: 2 to 5.

Item 3. The preventive or therapeutic agent according to Item 2, wherein the DE loop sequence is the amino acid sequence (a).

Item 4. The oligopeptide according to Item 2 or 3, wherein in the amino acid sequence (d), the leucine residue at the N-terminus of SEQ ID NOs: 2 and 4, and the leucine residue that is the fourth amino acid from the N-terminus of SEQ ID NOs: 3 and 5, are not substituted or deleted.

Item 5. The preventive or therapeutic agent according to any one of Items 1 to 4, wherein the amino acid sequence of the oligopeptide contains a β-strand E sequence of RANKL protein placed adjacent to the C-terminal side of the DE loop sequence.

Item 6. The preventive or therapeutic agent according to Item 5, wherein the β-strand E sequence is the following amino acid sequence (e) or (f):
  (e) the amino acid sequence represented by any one of SEQ ID NOs: 6 to 9, or
  (f) an amino acid sequence with substitution, deletion, addition, or insertion of one to three amino acids in the amino acid sequence represented by any one of SEQ ID NOs: 6 to 9.

Item 7. The preventive or therapeutic agent according to any one of Items 1 to 6, wherein the amino acid sequence of the oligopeptide is free from a CD loop sequence of RANKL protein.

Item 8. The preventive or therapeutic agent according to any one of Items 1 to 7, wherein the amino acid sequence of the oligopeptide is the following amino acid sequence (i) or (j):
  (i) the amino acid sequence represented by any one of SEQ ID NOs: 12 to 20, or (j) an amino acid sequence with substitution, deletion, addition, or insertion of one to three amino acids in the amino acid sequence represented by any one of SEQ ID NOs: 12 to 20.

Item 9. The preventive or therapeutic agent according to any one of Items 1 to 7, wherein the amino acid sequence of the oligopeptide is the following amino acid sequence (i') or (j'):
(i') the amino acid sequence represented by SEQ ID NO: 12, 15 or 16, or
(j') an amino acid sequence with substitution, deletion, addition, or insertion of one to three amino acids in the amino acid sequence represented by any one of SEQ ID NO: 12, 15 or 16.

Item 10. The preventive or therapeutic agent according to any one of Items 1 to 9, wherein the oligopeptide has a length of 40 amino acid residues or less.

Item 11. The preventive or therapeutic agent according to Item 10, wherein the oligopeptide has a length of 30 amino acid residues or less.

Item 12. The preventive or therapeutic agent according to any one of Items 1 to 11, wherein the inflammatory skin disease is at least one member selected from the group consisting of psoriasis, atopic dermatitis, arthritis, lichen planus, palmoplantar pustulosis, and bullosis.

Item 13. The preventive or therapeutic agent according to any one of Items 1 to 12, wherein the inflammatory skin disease is at least one member selected from the group consisting of psoriasis and atopic dermatitis.

Item 14. An inhibitor of at least one pathway selected from the group consisting of Toll-like receptor 7 pathway and Toll-like receptor 8 pathway, the inhibitor comprising an oligopeptide consisting of an amino acid sequence containing a DE loop sequence of RANKL protein and a β-strand D sequence of RANKL protein placed adjacent to the N-terminal side of the DE loop sequence,
wherein the DE loop sequence is the following amino acid sequence (a) or (b):
(a) the amino acid sequence represented by SEQ ID NO: 1, or
(b) an amino acid sequence with substitution, deletion, addition, or insertion of one amino acid in the amino acid sequence represented by SEQ ID NO: 1.

Item 15. A drug for external use for preventing or treating an inflammatory skin disease, the drug comprising an oligopeptide consisting of an amino acid sequence containing a DE loop sequence of RANKL protein and a β-strand D sequence of RANKL protein placed adjacent to the N-terminal side of the DE loop sequence,
wherein the DE loop sequence is the following amino acid sequence (a) or (b):
(a) the amino acid sequence represented by SEQ ID NO: 1, or
(b) an amino acid sequence with substitution, deletion, addition, or insertion of one amino acid in the amino acid sequence represented by SEQ ID NO: 1.

Item 16. A method for preventing or treating an inflammatory skin disease, the method comprising administering an oligopeptide consisting of an amino acid sequence containing a DE loop sequence of RANKL protein and a β-strand D sequence of RANKL protein placed adjacent to the N-terminal side of the DE loop sequence,
wherein the DE loop sequence is the following amino acid sequence (a) or (b):
(a) the amino acid sequence represented by SEQ ID NO: 1, or
(b) an amino acid sequence with substitution, deletion, addition, or insertion of one amino acid in the amino acid sequence represented by SEQ ID NO: 1.

Item 17. An oligopeptide for use as a preventive or therapeutic agent for an inflammatory skin disease, the oligopeptide consisting of an amino acid sequence containing a DE loop sequence of RANKL protein and a β-strand D sequence of RANKL protein placed adjacent to the N-terminal side of the DE loop sequence,
wherein the DE loop sequence is the following amino acid sequence (a) or (b):
(a) the amino acid sequence represented by SEQ ID NO: 1, or
(b) an amino acid sequence with substitution, deletion, addition, or insertion of one amino acid in the amino acid sequence represented by SEQ ID NO: 1.

Item 18. Use of an oligopeptide for the manufacture of a preventive or therapeutic agent for an inflammatory skin disease, the oligopeptide consisting of an amino acid sequence containing a DE loop sequence of RANKL protein and a β-strand D sequence of RANKL protein placed adjacent to the N-terminal side of the DE loop sequence,
wherein the DE loop sequence is the following amino acid sequence (a) or (b):
(a) the amino acid sequence represented by SEQ ID NO: 1, or
(b) an amino acid sequence with substitution, deletion, addition, or insertion of one amino acid in the amino acid sequence represented by SEQ ID NO: 1.

Advantageous Effects of Invention

The present invention provides a preventive or therapeutic agent for an inflammatory skin disease, such as psoriasis, the agent comprising an oligopeptide as an active ingredient.

Although RANKL protein activates osteoclasts, the oligopeptide used in the present invention (hereinafter sometimes referred to as "the RANKL peptide"), which is from RANKL protein, does not have such a property; rather the oligopeptide can inhibit the activation of osteoclasts by RANKL protein. Therefore, the use of this oligopeptide can prevent or treat inflammatory skin diseases while further reducing the osteoclast activation.

The oligopeptide used in the present invention has excellent stability and can maintain higher activity even after long-term storage.

The preventive or therapeutic agent of the present invention, which comprises an oligopeptide as an active ingredient, can be provided at a lower cost than existing therapeutic agents containing an antibody as an active ingredient (e.g., infliximab, adalimumab, and ustekinumab). Therefore, the present invention can also contribute to a reduction in medical costs. Inflammatory skin diseases, such as psoriasis, have currently been increasing, and reducing medical costs is an important issue.

BRIEF DESCRIPTION OF DRAWINGS

In FIGS. 8A and 8B, the vertical axis represents the value obtained by dividing the mRNA expression level of the measurement object by the GAPDH mRNA expression level. In FIG. 8C, the vertical axis represents the absorbance (which indicates the amount of p65 in the nuclear protein, binding to DNA having the NFκB-binding sequence) measured by the TransAM NFkB p65 kit.

DESCRIPTION OF EMBODIMENTS

1. Definition

Figure 1:
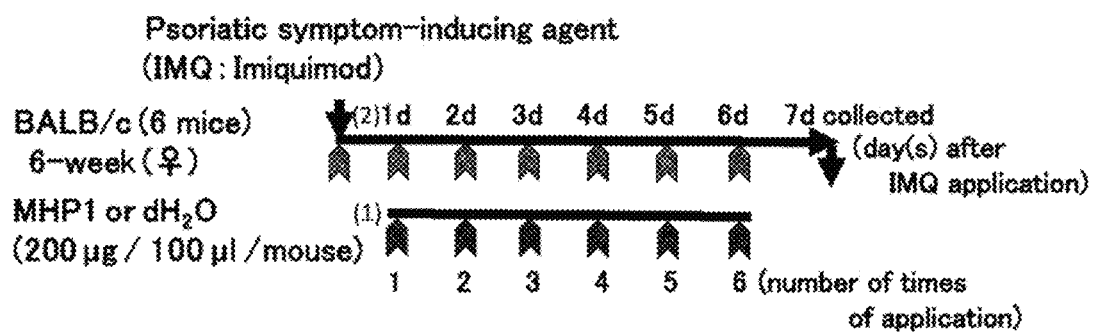
FIG. 1 shows the dosing schedule in the analysis of preventive and therapeutic effects on inflammatory skin diseases (Example 1).

In the present specification, the amino acid sequences are all represented by single letters.

In the present specification, the terms "containing," "comprising," and "having" include the concepts of "containing," "including," "consisting essentially of," and "consisting only of."

The "identity" of amino acid sequences refers to the degree of identicalness of amino acid sequences in two or more comparable amino acid sequences. Therefore, as the identity of two amino acid sequences is higher, the identity or similarity of the sequences is higher. The level of amino acid sequence identity is determined, for example, by FASTA, which is a tool for sequence analysis, using default parameters. Alternatively, the level of amino acid sequence identity can be determined using the algorithm BLAST by Karlin and Altschul (Karlin S, Altschul SF, "Methods for assessing the statistical significance of molecular sequence features by using general scoring schemes," Proc Natl Acad Sci USA. 87: 2264-2268 (1990); and Karlin S, Altschul SF, "Applications and statistics for multiple high-scoring segments in molecular sequences," Proc Natl Acad Sci USA. 90: 5873-7 (1993)). A program called "BLASTX," which is based on this BLAST algorithm, has been developed. Specific procedures of these analysis methods are known, and reference may be made to the website (http://www.ncbi.nlm.nih.gov/) of the National Center of Biotechnology Information (NCBI). The "identity" of base sequences is also defined accordingly.

In the present specification, "conservative substitution" means that an amino acid residue is substituted with another amino acid residue having a similar side chain. For example, conservative substitutions include substitutions with amino acid residues having basic side chains, such as lysine, arginine, and histidine. Other examples of conservative substitutions include substitutions with the following amino acid residues: amino acid residues with acidic side chains, such as asparagic acid and glutamic acid; amino acid residues with uncharged polar side chains, such as glycine, asparagine, glutamine, serine, threonine, tyrosine, and cysteine; amino acid residues with nonpolar side chains, such as alanine, valine, leucine, isoleucine, proline, phenylalanine, methionine, and tryptophan; amino acid residues with β-branched side chains, such as threonine, valine, and isoleucine; and amino acid residues with aromatic side chains, such as tyrosine, phenylalanine, tryptophan, and histidine.

2. Oligopeptide

The following describes an oligopeptide consisting of an amino acid sequence containing a DE loop sequence of RANKL protein and a β-strand D sequence of RANKL protein placed adjacent to the N-terminal side of the DE loop sequence (which may be referred to as "the oligopeptide of the present invention" in the present specification).

The DE loop sequence of RANKL protein may be the following amino acid sequence (a) or (b):
  (a) the amino acid sequence represented by SEQ ID NO: 1, or
  (b) an amino acid sequence with substitution, deletion, addition, or insertion of one amino acid in the amino acid sequence represented by SEQ ID NO: 1.

The β-strand D sequence of RANKL protein is not particularly limited, as long as it is, among the amino acid sequences of RANKL protein, an amino acid sequence that forms β-strand D. The organism species from which the β-strand D sequence is derived is not particularly limited. Examples include various mammals, such as humans, monkeys, mice, rats, dogs, cats, and rabbits. Among these, humans, monkeys, mice, rats, etc., are preferable; humans, mice, etc., are more preferable; and humans are even more preferable. β-strand D sequences of various organism species are known. For example, those of mice and rats are disclosed in NPL 1, NPL 2, etc. Even if a β-strand D sequence derived from a certain organism species is not known, the sequence can be easily determined based on known information (e.g., NPL 1 and NPL 2). Specific examples of the β-strand D sequence of RANKL protein include the amino acid sequence represented by SEQ ID NO: 2 (part of a β-strand D sequence of mouse-derived RANKL protein), the amino acid sequence represented by SEQ ID NO: 3 (a β-strand D sequence of mouse-derived RANKL protein), the amino acid sequence represented by SEQ ID NO: 4 (part of a β-strand D sequence of human-derived RANKL protein), the amino acid sequence represented by SEQ ID NO: 5 (a β-strand D sequence of human-derived RANKL protein), and the like. The β-strand D sequence may be mutated as long as the oligopeptide of the present invention can exhibit a preventive or therapeutic effect on inflammatory skin diseases.

In SEQ ID NOs: 2 to 5, the leucine residues at the N-terminus of SEQ ID NOs: 2 and 4, and the leucine residue that is the fourth amino acid from the N-terminus of SEQ ID NOs: 3 and 5, are important for exhibiting preventive and therapeutic effects on inflammatory skin diseases. In the β-strand D sequence, it is preferable that these leucine residues be not mutated.

The β-strand D sequence of RANKL protein is preferably the following amino acid sequence (c) or (d):
  (c) the amino acid sequence represented by any one of SEQ ID NOs: 2 to 5, or
  (d) an amino acid sequence with substitution, deletion, addition, or insertion of one to three amino acids in the amino acid sequence represented by any one of SEQ ID NOs: 2 to 5.

In (d) above, the number of mutated (substituted, deleted, added, or inserted) amino acids is preferably 1 to 2, and more preferably 1.

The amino acid sequence (d) is preferably the following amino acid sequence (d'):

(d') an amino acid sequence in which one to three amino acids are added to the N-terminus or C-terminus (preferably N-terminus) of the amino acid sequence represented by any one of SEQ ID NOs: 2 to 5.

In the sequence (d'), the number of amino acids added is preferably 1 to 2, and more preferably 1.

The phrase "placed adjacent to the N-terminal side" indicates that the amino acid at the N-terminus of the DE loop sequence and the amino acid at the C-terminus of the above β-strand D sequence are linked by a peptide bond.

The amino acid sequence of the oligopeptide of the present invention may contain other sequences than those described above, as long as the oligopeptide of the present invention can exhibit a preventive or therapeutic effect on inflammatory skin diseases. The other sequences are not particularly limited, but are preferably determined from the viewpoint, for example, that the intracellular half-life is longer. The hydrophilicity of the oligopeptide and the intracellular half-life can be presumed based on various websites (e.g., ExPASy (http://web.expasy.org/protparam/)). When ExPASy is used regarding hydrophilicity, it is preferable to design a sequence so that the "grand average of hydropathicity" shows a negative value.

The other sequences preferably include a β-strand E sequence of RANKL protein. The β-strand E sequence is preferably placed adjacent to the C-terminal side of the DE loop sequence. The phrase "adjacent to the C-terminal side" indicates that the amino acid at the C-terminus of the DE loop sequence and the amino acid at the N-terminus of the above β-strand E sequence are linked by a peptide bond.

The β-strand E sequence of RANKL protein is not particularly limited, as long as it is, among the amino acid sequences of RANKL protein, an amino acid sequence that forms β-strand E. The organism species from which the β-strand E sequence is derived is not particularly limited. Examples include various mammals, such as humans, monkeys, mice, rats, dogs, cats, and rabbits. Among these, humans, monkeys, mice, rats, etc., are preferable; humans, mice, etc., are more preferable; and humans are even more preferable. β-strand E sequences of various organism species are known. For example, those of mice and rats are disclosed in NPL 1, NPL 2, etc. Even if a β-strand E sequence derived from a certain organism species is not known, the sequence can be easily determined based on known information (e.g., NPL 1 and NPL 2). Specific examples of the β-strand E sequence of RANKL protein include the amino acid sequence represented by SEQ ID NO: 6 (a β-strand E sequence of mouse-derived RANKL protein), the amino acid sequence represented by SEQ ID NO: 7 (part of a β-strand E sequence of mouse-derived RANKL protein), the amino acid sequence represented by SEQ ID NO: 8 (a β-strand E sequence of human-derived RANKL protein), the amino acid sequence represented by SEQ ID NO: 9 (part of a β-strand E sequence of human-derived RANKL protein), and the like. The β-strand E sequence may be mutated as long as the oligopeptide of the present invention can exhibit a preventive or therapeutic effect on inflammatory skin diseases.

The β-strand E sequence of RANKL protein is preferably the following amino acid sequence (e) or (f):

(e) the amino acid sequence represented by any one of SEQ ID NOs: 6 to 9, or (d) an amino acid sequence with substitution, deletion, addition, or insertion of one to three amino acids in the amino acid sequence represented by any one of SEQ ID NOs: 6 to 9.

In (f) above, the number of mutated (substituted, deleted, added, or inserted) amino acids is preferably 1 to 2, and more preferably 1.

The amino acid sequence of the oligopeptide of the present invention is preferably free from a CD-loop sequence of RANKL protein.

The CD loop sequence of RANKL protein is not particularly limited, as long as it is, among the amino acid sequences of RANKL protein, an amino acid sequence that forms a CD loop. The organism species from which the CD loop sequence is derived is not particularly limited. Examples include various mammals, such as humans, monkeys, mice, rats, dogs, cats, and rabbits. Among these, humans, monkeys, mice, rats, etc., are preferable; humans, mice, etc., are more preferable; and humans are even more preferable. CD loop sequences of various organism species are known. For example, those of mice and rats are disclosed in NPL 1, NPL 2, etc. Even if a CD loop sequence derived from a certain organism species is not known, the sequence can be easily determined based on known information (e.g., NPL 1 and NPL 2). Specific examples of the CD loop sequence of RANKL protein include the amino acid sequence represented by SEQ ID NO: 10 (a CD loop sequence of mouse-derived RANKL protein), the amino acid sequence represented by SEQ ID NO: 11 (a CD loop sequence of human-derived RANKL protein), and the like.

The CD loop sequence of RANKL protein is preferably the following amino acid sequence (g) or (h):

(g) the amino acid sequence represented by SEQ ID NO: 10 or 11, or (h) an amino acid sequence with substitution, deletion, addition, or insertion of one to three amino acids in the amino acid sequence represented by SEQ ID NO: 10 or 11.

In (h) above, the number of mutated (substituted, deleted, added, or inserted) amino acids is preferably 1 to 2, and more preferably 1.

The length of the oligopeptide of the present invention is not particularly limited as long as it is a general length as an oligopeptide. The length is, for example, 50 amino acid residues or less, preferably 40 amino acid residues or less, more preferably 35 amino acid residues or less, still more preferably 30 amino acid residues or less, still more preferably 25 amino acid residues or less, still even more preferably 20 amino acid residues or less, and still further more preferably 18 amino acid residues or less. The length is, for example, 11 amino acid residues or more, preferably 13 amino acid residues or more, and more preferably 15 amino acid residues or more. The length is preferably, for example, 11 to 50 amino acid residues, more preferably 11 to 40 amino acid residues, still more preferably 13 to 30 amino acid residues, still more preferably 13 to 20 amino acid residues, and even more preferably 15 to 18 amino acid residues.

The amino acid sequence of the oligopeptide of the invention is preferably the following amino acid sequence (i) or (j):

(i) the amino acid sequence represented by any one of SEQ ID NOs: 12 to 20, or (j) an amino acid sequence with substitution, deletion, addition, or insertion of one to three amino acids in the amino acid sequence represented by any one of SEQ ID NOs: 12 to 20.

The amino acid sequence of the oligopeptide of the invention is more preferably the following amino acid sequence (i') or (j'):
(i') the amino acid sequence represented by SEQ ID NO: 12, 15 or 16, or
(j') an amino acid sequence with substitution, deletion, addition, or insertion of one to three amino acids in the amino acid sequence represented by SEQ ID NO: 12, 15 or 16.

In (j) and (j') above, the number of mutated (substituted, deleted, added, or inserted) amino acids is preferably 1 to 2, and more preferably 1.

The oligopeptide of the present invention may be chemically modified as long as it can exhibit a preventive or therapeutic effect on inflammatory skin diseases.

The C-terminus of the oligopeptide of the present invention may be a carboxyl group (—COOH), carboxylate (—COO⁻), amide (—CONH$_2$), or ester (—COOR).

Examples of R in the ester include $C_{1-6}$ alkyl groups, such as methyl, ethyl, n-propyl, isopropyl, and n-butyl; $C_{3-8}$ cycloalkyl groups, such as cyclopentyl and cyclohexyl; $C_{6-12}$ aryl groups, such as phenyl and α-naphthyl; phenyl-$C_{1-2}$ alkyl groups, such as benzyl and phenethyl; $C_{7-14}$ aralkyl groups, such as α-naphthyl-$C_{1-2}$ alkyl groups (e.g., α-naphthyloxymethyl); pivaloyloxymethyl groups; and the like.

Furthermore, the oligopeptide of the present invention also includes those in which the amino group of the N-terminal amino acid residue is protected by a protecting group (e.g., $C_{1-6}$ acyl groups such as $C_{1-6}$ alkanoyl, including formyl and acetyl groups), etc.

The chemical modification is preferably amidation at the C-terminus, protection at the N-terminus with an acetyl group, and the like. In particular, an oligopeptide with acetylated N-terminus is preferable for its excellent activity. In terms of stability, an oligopeptide with amidated C-terminus and acetylated N-terminus is more preferable for its excellent stability. Examples of particularly preferred oligopeptides include MHP1 with amidated C-terminus and acetylated N-terminus, and MHP4 with amidated C-terminus and acetylated N-terminus.

A known substance for modification may be further added to the oligopeptide of the present invention, for the purpose of improving the stability, pharmacokinetics, bioavailability, etc., of drugs. Such substances for modification include, for example, polyethylene glycol chains.

The oligopeptide of the present invention includes those having various forms, such as linear oligopeptides, branched oligopeptides, and cyclic oligopeptides, with linear oligopeptides being preferable. The oligopeptide of the present invention may be crosslinked by or based on a known means as long as it can exhibit a preventive or therapeutic effect on inflammatory skin diseases.

The oligopeptide of the present invention may be in the form of a pharmaceutically acceptable salt with an acid or a base. The salt is not particularly limited, as long as it is a pharmaceutically acceptable salt. Acid salts and basic salts can both be employed. Examples of acid salts include inorganic acid salts, such as hydrochloride, hydrobromate, sulfate, nitrate, and phosphate; organic acid salts, such as acetate, propionate, tartrate, fumarate, maleate, malate, citrate, methanesulfonate, and p-toluenesulfonate; amino acid salts, such as aspartate and glutamate; and the like. Examples of basic salts include alkali metal salts, such as sodium salt and potassium salt; alkaline earth metal salts, such as calcium salt and magnesium salt; and the like.

The oligopeptide of the present invention may be in the form of a solvate. The solvent is not particularly limited, as long as it is pharmaceutically acceptable. Examples include water, ethanol, glycerol, acetic acid, and the like.

The oligopeptide of the present invention can be produced by a known peptide synthesis method, depending on its amino acid sequence.

3. Application

The oligopeptide of the present invention exhibits a preventive or therapeutic effect on inflammatory skin diseases, as well as an inhibitory effect on at least one pathway selected from the group consisting of Toll-like receptor 7 pathway and Toll-like receptor 8 pathway (more specifically, an inhibitory effect on an inflammatory response elicited through this pathway (or these pathways)); thus, the oligopeptide of the present invention can be used as an active ingredient of a preventive or therapeutic agent for inflammatory skin diseases or an inhibitor of at least one pathway selected from the group consisting of Toll-like receptor 7 pathway and Toll-like receptor 8 pathway (in the present specification, these may be collectively referred to as "the agent of the present invention"). The agent of the present invention can be used in various fields, such as medicine and cosmetics. The agent of the present invention may be applied to (e.g., administered to, ingested by, inoculated into) animals and humans directly or as various compositions in combination with conventional components.

In the agent of the present invention, the oligopeptides of the present invention may be used alone or in a combination of two or more.

Examples of inflammatory skin diseases include psoriasis, atopic dermatitis, arthritis, lichen planus, palmoplantar pustulosis, bullosis, and the like. Among these, psoriasis, atopic dermatitis, and the like are preferable, and psoriasis is more preferable.

The content of the active ingredient in the agent of the present invention can be suitably determined taking into consideration the type of target disease, the intended therapeutic effect, the administration method, the treatment period, the patient's age, the patient's body weight, etc. For example, the content of the active ingredient in the agent of the present invention can be about 0.0001 parts by weight to 100 parts by weight based on the entire agent of the present invention.

The administration form of the agent of the present invention is not particularly limited as long as a desired effect is exhibited. The agent can be administered to mammals, including humans through an administration route, either peroral or parenteral administration, (e.g., intravenous injection, intramuscular injection, subcutaneous administration, rectal administration, transdermal administration, and local administration). The administration form is preferably parenteral administration, more preferably local administration, transdermal administration, and the like. The dosage form and production method of the agent for peroral or parenteral administration are well known to those skilled in the art, and the agent in any dosage form can be produced in accordance with conventional methods, for example, by mixing the active ingredient with a pharmaceutically acceptable carrier and the like.

The dosage form for parenteral administration includes drugs for external use (e.g., ointments, cataplasms, lotions, creams, and gels), suppositories, inhalants, eye drops, eye ointments, nasal drops, ear drops, liposome drugs, injectable drugs (e.g., drip-injectable drugs, intravenously injectable drugs, intramuscularly injectable drugs, subcutaneously injectable drugs, and intradermally injectable drugs), and the like. For example, an injectable drug can be prepared by dissolving the oligopeptide of the present invention in injectable distilled water; and a solubilizing agent, a buffer, a pH adjuster, a tonicity agent, a soothing agent, a preservative, a stabilizer, and the like can be optionally added thereto. The agent of the present invention may in the form of a freeze-dried formulation that is prepared when needed.

The agent of the present invention may further comprise other medical agents effective in treatment or prevention of diseases. The agent of the present invention may also optionally contain components such as a sterilizer, an antiphlogistic, a cellular stimulant, vitamins, and an amino acid.

For the carriers used in formulating the agent of the present invention, an excipient, a binder, a disintegrant, a lubricant, a colorant, and a flavoring agent typically used in this technical field can be used; and a stabilizer, an emulsifier, an absorption promoter, a surfactant, a pH adjuster, an antiseptic, an antioxidant, a filler, a moisture agent, a surface activation agent, a dispersant, a buffer, a preservative, a solubilizing agent, a soothing agent, and the like can also optionally be used.

The dose of the agent of the present invention can be determined taking into consideration various factors, such as the administration route, the type of disease, the degree of symptoms, the patient's age, gender, body weight, severity of disease, pharmacological findings such as pharmacokinetics and toxicological characteristics, use or non-use of a drug delivery system, and whether the agent is administered as part of a combinational drug with other drugs. For example, the dose of the agent of the present invention can be about 1 µg/kg (body weight) to 10 g/kg (body weight) per day. The administration schedule of the agent of the present invention can also be determined in consideration of the same factors as the dose. For example, the dose per day as described above can be administered 1 to 4 times a day to a month.

The agent of the present invention is preferably used externally. One embodiment of the present invention includes a drug for external use that is for prevention or treatment of an inflammatory skin disease, the drug comprising the oligopeptide of the present invention. The drug for external use of the present invention encompasses a preparation for application to the skin, a preparation for application to the rectum, a preparation for application to the vagina, a preparation for application to the eye, a preparation for application to the ear, and a preparation for application to the nose. The dosage form may be, for example, ointments, creams, gels, solutions (e.g., lotions and liniments), patches (cataplasms, tapes), sprays, aerosols, suppositories, eye ointments, eye drops, nasal drops, and ear drops. The drug for external use can be administered directly to the lesion. The drug for external use of the present invention has an excellent preventive and therapeutic effect on inflammatory diseases and is safe in terms of side effects.

In a preferable embodiment (Embodiment 1), the drug for external use of the present invention is an ointment, a cream, a gel, or a solution, and in a particularly preferable embodiment, the drug for external use of the present invention is an ointment or a cream. The base is preferably, but not particularly limited to, a hydrophilic base, such as hydrophilic petrolatum or hydrophilic cream. The oligopeptide of the present invention may be mixed with a base as is, and is preferably mixed with a base in a state of being dissolved in a solvent. Examples of the solvent include water and various organic solvents, such as glycol ether, alcohol, and ether, with glycol ether being preferable.

The content of the active ingredient in the drug for external use according to Embodiment 1 is preferably 0.00001 to 2%, 0.00005 to 1%, 0.0001 to 0.5%, 0.0003 to 0.1%, 0.0005 to 0.05%, and 0.0008 to 0.01%, more preferably 0.001 to 0.005%, and still more preferably 0.002 to 0.003%. In this case, it is possible to use relatively short RANKL peptide (preferably 15 to 20 amino acid residues in length, more preferably 15 to 18 amino acid residues in length, and even more preferably 15 to 16 amino acid residues in length) (e.g., MHP4) preferably containing a DE loop sequence and a β-strand D sequence. According to this embodiment, the desired effects can be efficiently exhibited even at a very low concentration of RANKL peptide.

In another embodiment, the content of the active ingredient in the drug for external use according to Embodiment 1 is preferably 0.00001 to 2%, 0.00005 to 1%, 0.0001 to 0.5%, 0.0003 to 0.1%, 0.001 to 0.05%, and 0.005 to 0.03%, and more preferably 0.008 to 0.025%. In this case, it is possible to use relatively short RANKL peptide (preferably 15 to 40 amino acid residues in length, more preferably 20 to 35 amino acid residues in length, more preferably 25 to 35 amino acid residues in length, and even more preferably 27 to 33 amino acid residues in length) (e.g., MHP1) preferably containing a DE loop sequence and a β-strand D sequence (and more preferably further containing a β-strand E sequence). According to this embodiment, the desired effects can be efficiently exhibited even at a very low concentration of RANKL peptide.

EXAMPLES

The present invention is described in detail below based on Examples; however, the present invention is not limited to these Examples.

Reference Example 1: Synthesis of Oligopeptides 1

Synthesis of oligopeptides consisting of the amino acid sequences shown in Table 1 was entrusted to ILS Inc. It was confirmed by HPLC and MS that oligopeptides with the desired sequences were synthesized with high purity. Amino acid residues in these peptides are all L-forms. Hereinafter, these peptides are also generically referred to as "the RANKL peptide." The amino acid sequence of MHP1 is represented by SEQ ID NO: 12, the amino acid sequence of MHP2 is represented by SEQ ID NO: 13, the amino acid sequence of MHP3 is represented by SEQ ID NO: 14, the amino acid sequence of MHP4 is represented by SEQ ID NO: 15, the amino acid sequence of hMHP4 is represented by SEQ ID NO: 16, the amino acid sequence of MHP5 is represented by SEQ ID NO: 17, the amino acid sequence of MHP6 is represented by SEQ ID NO: 18, the amino acid sequence of MHP12 is represented by SEQ ID NO: 19, and the amino acid sequence of MHP13 is represented by SEQ ID NO: 20.

TABLE 1

| Name | Sequence | Species origin | Number of amino acids |
|---|---|---|---|
| MHP1 | LMVYVVKTSIKIPSSHNLMKGGSTKNWSGN | Mouse | 30 |
| MHP2 | DYLQLMVYVVKTSIKIPSSHNLMKGGSTKN | Mouse | 30 |
| MHP3 | HETSGSVPADYLQLMVYVVKTSIKIPSS | Mouse | 28 |

TABLE 1-continued

| Name | Sequence | Species origin | Number of amino acids |
|---|---|---|---|
| MHP4 | LMVYVVKTSIKIPSS | Mouse | 15 |
| hMHP4 | LMVYVTKTSIKIPSS | Human | 15 |
| MHP5 | LMVYVVKTSIKIPSSHNLMKGG | Mouse | 22 |
| MHP6 | LMVYVTKTSIKIPSSHTLMKGGSTKYWSGN | Human | 30 |
| MHP12 | LMVYVVKTSIKIPSSHNLMKGGS | Mouse | 23 |
| MHP13 | LMVYVVKTSIKIPSSHNLMKGGSTKN | Mouse | 26 |

Example 1: Analysis 1 of Preventive and Therapeutic Effects on Inflammatory Skin Diseases Whether the RANKL peptide (MHP1) improved psoriatic symptoms caused by the administration of imiquimod (IMQ), which is a psoriatic symptom-inducing agent, was examined. Specifically, the following procedure was performed according to the dosing schedule shown in FIG. 1.

As test animals, BALB/c 6-week-old female mice whose back hair was partially removed were prepared. 5% imiquimod (IMQ) was applied to the hair-removed portion in the back and ear of each mouse (62.5 mg per mouse) (day 0 (0 d)). One day later, (1) an MHP1 aqueous solution (200 µg/100 µL per mouse, n=2) or dH$_2$O (control, n=2) was individually applied to the back and ear, followed by the application of (2) 5% imiquimod (IMQ) (62.5 mg per mouse (day 1 (1 d)). Thereafter, items (1) and (2) above were applied every day for 5 days (day 2 to 6 (2 d to 6 d)).

Figure 2:
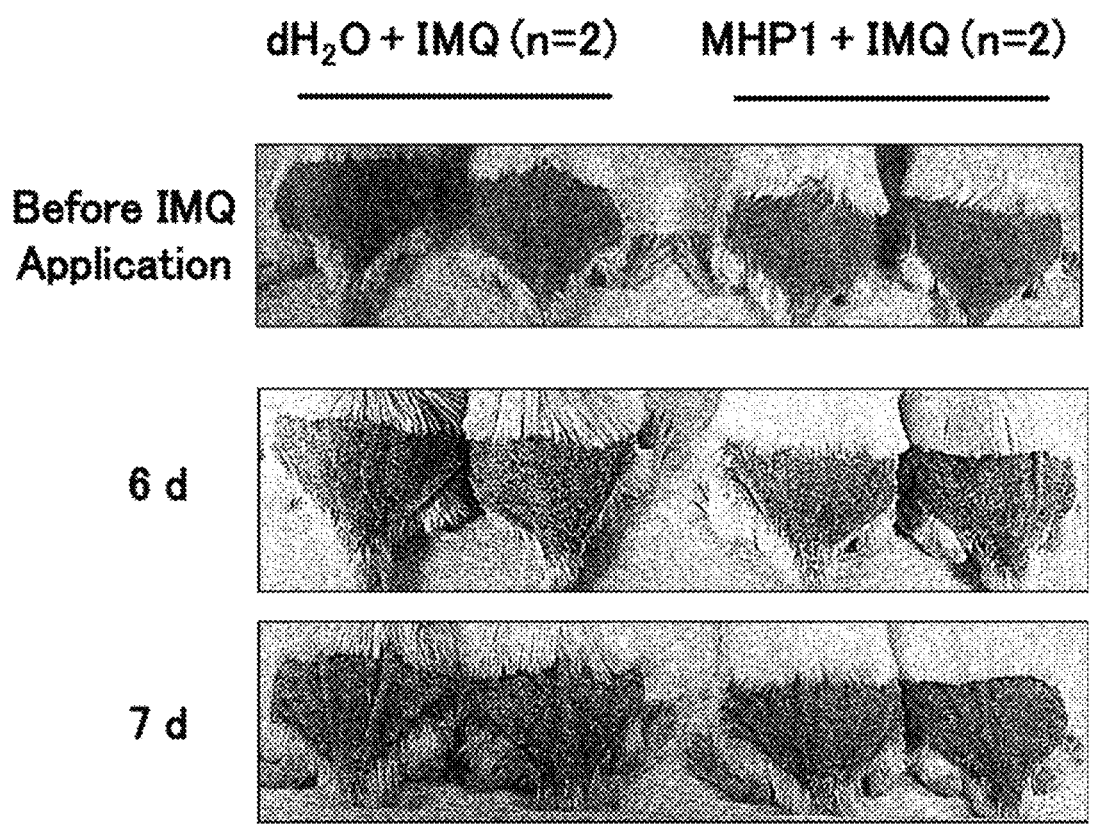
FIG. 2 shows the photographs of backs after administration in Analysis 1 of preventive and therapeutic effects on inflammatory skin diseases (Example 1). IMQ refers to imiquimod, which is a psoriatic symptom-inducing agent, dH₂O refers to a control group (MHP1 non-administration group), MHP1 refers to an MHP1 administration group, and 6 d and 7 d refer to Days 6 and 7 from the first imiquimod administration.

FIG. 2 shows the photographs of the observation sites in the backs of the mice.

Figure 3:
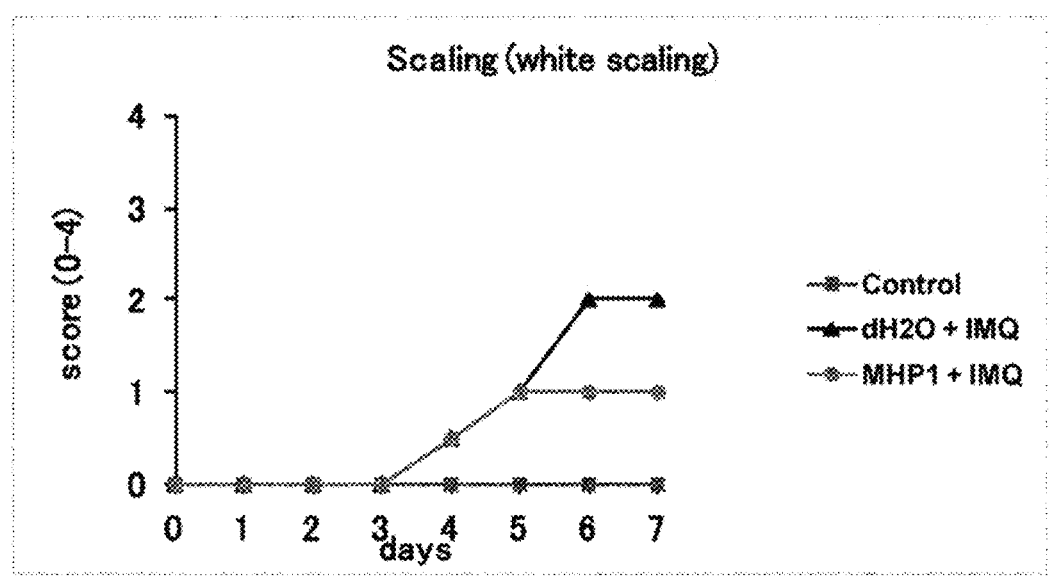
FIG. 3 shows the results of quantifying the degree of white scaling of each back in the analysis of preventive and therapeutic effects on inflammatory skin diseases (Example 1). The vertical axis represents the numerical value representing the degree of white scaling (evaluation criteria: none (0), mild (1), moderate (2), severe (3), and very severe (4)), and the horizontal axis represents the number of days elapsed from the first imiquimod administration. IMQ represents imiquimod, which is a psoriatic symptom-inducing agent, Control represents a case in which neither imiquimod nor MHP1 is administered, $dH_2O$ represents a control group (MHP1 non-administration group), and MHP1 represents an MHP1 administration group.

The degree of white scaling in the back was quantified in accordance with the description of the document (van der Fits, L. et al. Imiquimod-induced psoriasis-like skin inflammation in mice is mediated via the IL-23/IL-17 axis. J. Immunol. 182, 5836-45 (2009)) (evaluation criteria: none (0), mild (1), moderate (2), severe (3), and very severe (4)). FIG. 3 shows the results.

Figure 4:
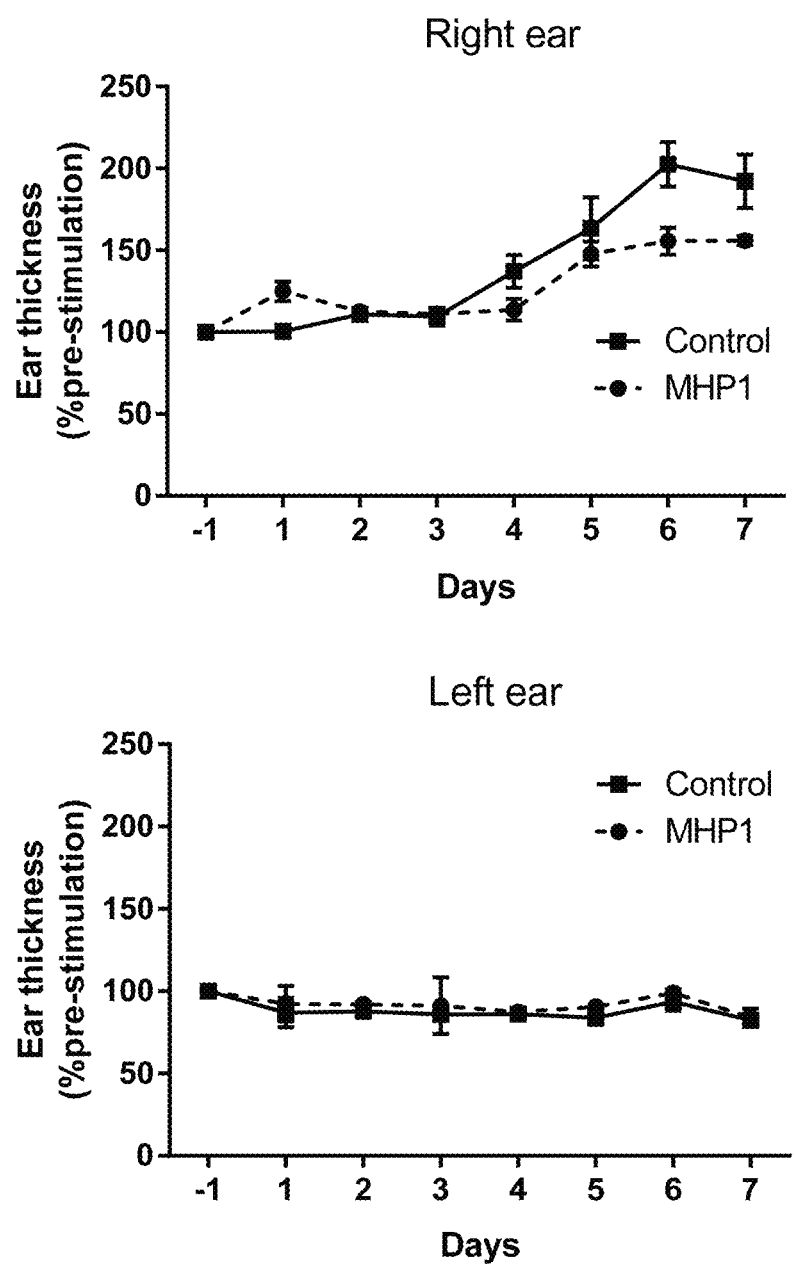
FIG. 4 shows the measurement results of ear thickness in the analysis of preventive and therapeutic effects on inflammatory skin diseases (Example 1). Right ear is a group to which imiquimod is administered and Left ear is a group to which imiquimod is not administered. In the horizontal axis, Day −1 represents the day before the first imiquimod administration, and others represent the number of days elapsed from the first imiquimod administration. The vertical axis represents the relative value of measured ear thickness that was calculated on the assumption that the ear thickness on Day −1 was 100%. Control represents an MHP1 non-administration group, and MHP1 represents an MHP1 administration group.

Additionally, the ear thickness was measured. FIG. 4 shows the results.

FIGS. 2 to 4 indicated that the administration of MHP1 improved psoriatic symptoms.

Example 2: Analysis 1 of Influence on TLR7/8 Signals (IL-6 and TFNα, Microglial Cells)

The influence of the RANKL peptide on the amount of proinflammatory cytokines (IL-6 and TFNα) secreted from microglial cells by the stimulation of imidazoquinoline resiquimod (R848 produced by Invitrogen), which is a TLR7/8 ligand, was examined. The specific examination procedures were as follows.

MG6 cells (mouse-derived microglial cell line) were cultured in a DMEM medium (+4% FBS) containing MHP1 or MHP4 (final concentration: 7.6, 15.3, or 30.5 µM) and R848 (final concentration: 1 µg/ml) or a DMEM medium (+4% FBS) containing R848 (final concentration: 1 µg/ml) alone for 24 hours by a standard method. After culturing, the concentrations of IL-6 and TNFα in the medium were measured by the ELISA method. In the Examples of the present application, the ELISA method was performed using a kit (Quantikine ELISA Mouse TNF-a or Quantikine ELISA Mouse IL-6, produced by R&D Systems). FIG. 5a (detected with IL-6) and FIG. 5b (detected with TNFα) show the results of the case containing MHP1, and FIG. 5c (detected with IL-6) shows the results of the case containing MHP4.

Figure 5:
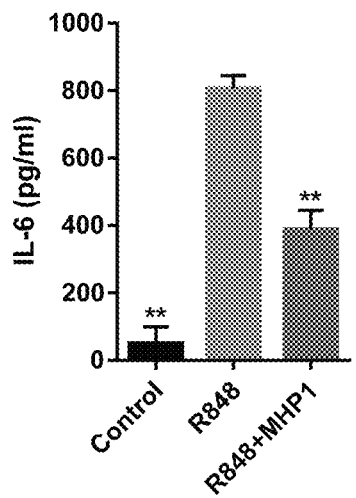
FIG. 5 shows the results of examining the influence of the RANKL peptide on the amount of proinflammatory cytokines (IL-6 or TNFα) secreted from microglial cells by imidazoquinoline resiquimod (R848), which is a ligand of TLR7/8 (Example 2). The vertical axis represents the IL-6 or TNFα concentration of the medium measured by ELISA. The concentration of MHP1 in the medium in FIGS. 5a and 5b is 30.5 μM. The numerical value of the horizontal axis in FIG. 5c represents the concentration of MHP4 in the medium, and Control represents a case in which neither R848 nor a RANKL peptide was contained in the medium. "**" indicates that the P-value relative to the case in which only R848 was contained (the second column from the left) was less than 0.01.
Figure 5:
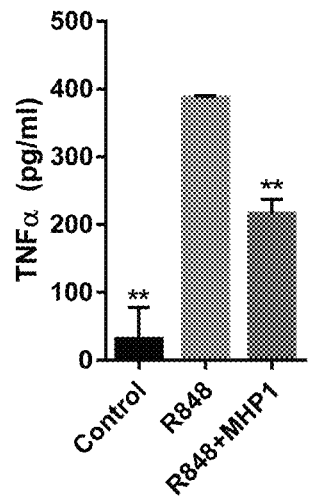
Figure 5:
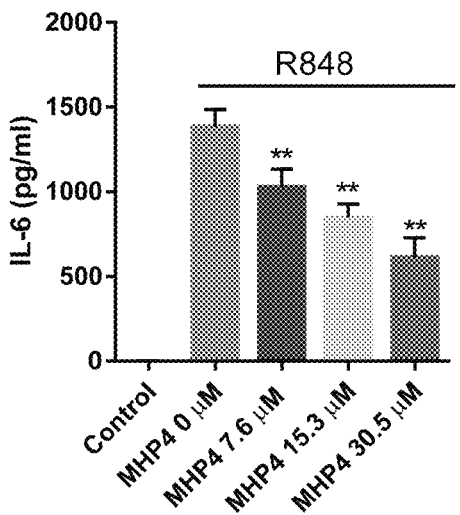

FIG. 5 revealed that the increase in the amount of proinflammatory cytokine (IL-6 and TNFα) secretion by R848 (comparison between the first column and the second column from the left) was suppressed by MHP1 and MHP4 (comparison between the second column and the third (FIGS. 5a and 5b) or the third to fifth columns (FIG. 5 c) from the left). This indicated that MHP1 and MHP4 suppressed the TLR7/8 signals.

Example 3: Analysis 2 of Influence on TLR7/8 Signals (IL-6 and Macrophage Cells)

The influence of the RANKL peptide on the amount of proinflammatory cytokines (IL-6) secreted from macrophage cells by the stimulation of a TLR7/8 ligand (R848) was examined. The specific examination procedures were as follows.

Figure 6:
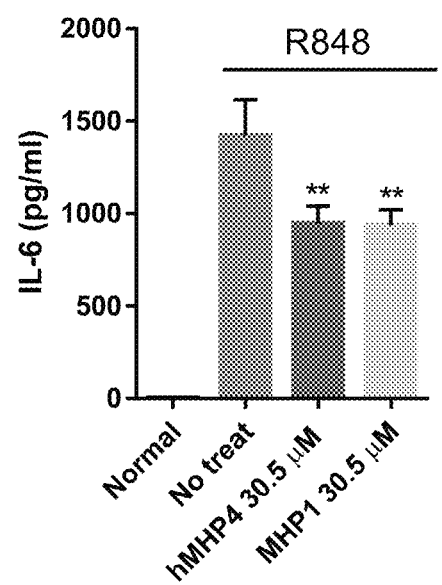
FIG. 6 shows the results of examining the influence of the RANKL peptide on the amount of proinflammatory cytokines (IL-6) secreted from macrophage cells by imidazoquinoline resiquimod (R848), which is a ligand of TLR7/8 (Example 3). The vertical axis represents the IL-6 concentration of the medium measured by ELISA. The numerical value of the horizontal axis represents the concentration of the RANKL peptide in the medium, and Normal represents a case in which neither R848 nor a RANKL peptide was contained in the medium. No treat represents a case in which only R848 was contained in the medium. "**" indicates that the P-value relative to the case in which only R848 was contained (the second column from the left) was less than 0.01.

THP-1 cells (human-derived macrophage cell line) were cultured in a DMEM medium (+4% FBS) containing MHP1 or hMHP4 (final concentration: 30.5 µM) and R848 (final concentration: 10 µg/ml) or a DMEM medium (+4% FBS) containing R848 (final concentration: 10 µg/ml) alone for 24 hours by a standard method. After culturing, the concentration of IL-6 in the medium was measured by the ELISA method. FIG. 6 shows the results.

FIG. 6 revealed that the increase in the amount of proinflammatory cytokine (IL-6) secretion by R848 (comparison between the first column and the second column from the left) was suppressed by MHP1 and hMHP4 (comparison between the second column and the third to fourth columns from the left). This indicated that MHP1 and hMHP4 suppressed the TLR7/8 signals. Additionally, MHP1 and hMHP4 had similar TLR7/8 signal suppression effects.

Example 4: Analysis 3 of Influence on TLR7/8 Signals (IL-12/23 and Macrophage Cells)

The influence of the RANKL peptide on the amount of proinflammatory cytokines (IL-12/23) secreted from macrophage cells by the stimulation of a TLR7/8 ligand (R848) was examined. The specific examination procedures were as follows.

Figure 7:
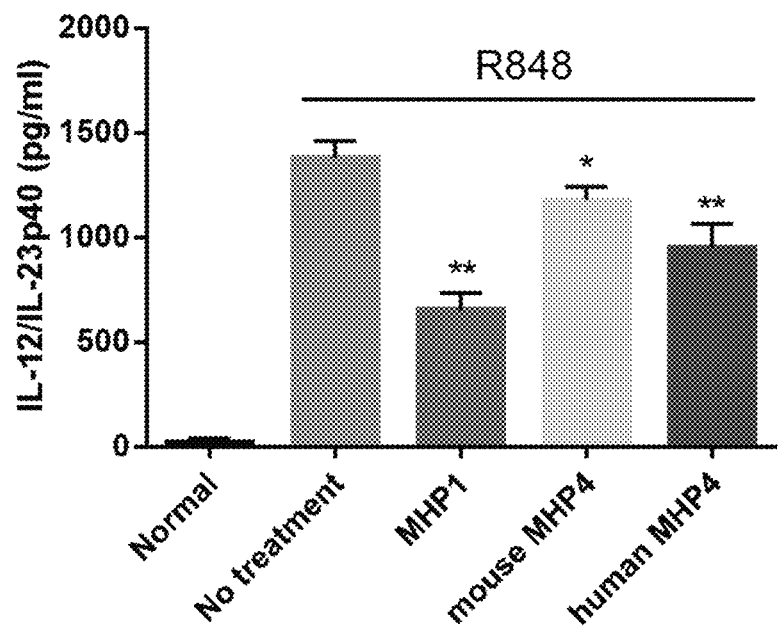
FIG. 7 shows the results of examining the influence of the RANKL peptide on the amount of proinflammatory cytokines (IL-12/23) secreted from macrophage cells by imidazoquinoline resiquimod (R848), which is a ligand of TLR7/8 (Example 4). The vertical axis represents the IL-12/23 concentration of the medium measured by ELISA. Control represents a case in which neither R848 nor a RANKL peptide was contained in the medium. No treatment represents a case in which only R848 was contained in the medium.

THP-1 cells (human-derived macrophage cell line) were cultured in a DMEM medium (+4% FBS) containing MHP1, MHP4, or hMHP4 (final concentration of each: 30.5 µM) and R848 (final concentration: 10 µg/ml) or a DMEM medium (+4% FBS) containing R848 (final concentration: 10 µg/ml) alone for 24 hours by a standard method. After culturing, the concentration of IL-12/23 in the medium was measured by the ELISA method using a kit (Quantikine ELISA kits, produced by R&D Systems). FIG. 7 shows the results.

FIG. 7 revealed that the increase in the amount of proinflammatory cytokine (IL-12/23) secretion by R848 (comparison between the first column and the second column from the left) was suppressed by the RANKL peptide (comparison between the second column and the third to fifth columns from the left). This indicated that the RANKL peptide suppressed the TLR7/8 signals.

Example 5: Analysis 1 of Influence of RANKL Peptide on Osteoclasts

It has recently been reported that the administration of RANKL protein to mice induces the activation of osteoclasts. Accordingly, the influence of the RANKL peptide on osteoclasts was examined. The specific examination procedures were as follows.

MHP1 (final concentration: 100 µg/ml) or RANKL protein (final concentration: 10 ng/ml) was added to a medium (DMEM medium (+4% FBS)) in which RAW264.7 cells were cultured, and the cells were collected after 10 minutes and 3 days.

Figure 8:
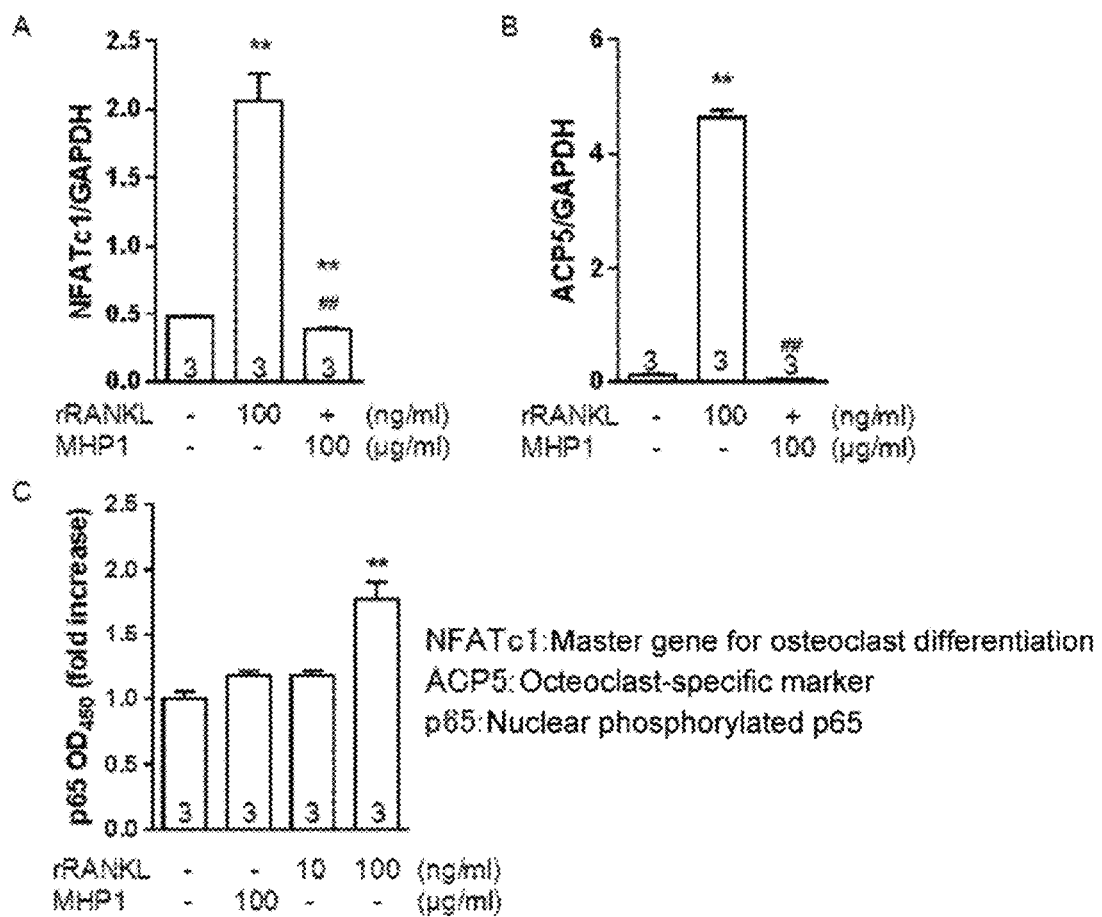
FIG. 8 shows the results of examining the influence of the RANKL peptide on osteoclasts (Example 5).

For the samples collected after 10 minutes, nuclear proteins of the cells were extracted using the Nuclear Extract Kit (Active Motif), and the degree of NFκB (p65) activation was measured by the TransAM NFkB p65 Kit (Active Motif). On the other hand, for the samples collected after 3 days, the mRNA expression levels of NFATc1 and ACP5 were analyzed by real-time RT-PCR. FIG. 8 shows the results.

FIG. 8 revealed that MHP1 slightly activated NFκB, but did not promote the expression of osteoclast-related mRNA.

Example 6: Analysis 2 of Influence of RANKL Peptide on Osteoclasts

Figure 9:
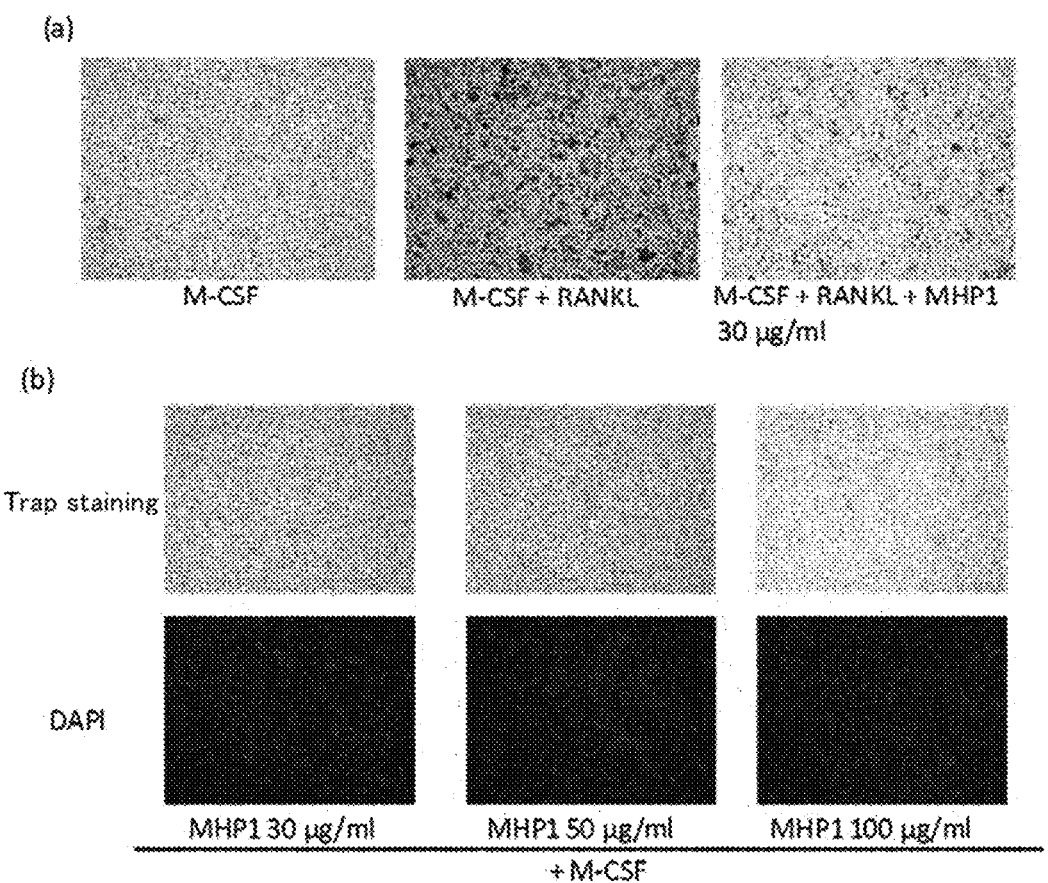
FIG. 9 shows the results of examining the influence of the RANKL peptide on osteoclasts (Example 6). (a) shows TRAP staining images of the A, B, and D groups, and (b) shows TRAP staining images (upper row) and nuclear staining images (lower row) of the C group.

Osteoclast Culture Kit V-2 (OSC33, produced by Cosmo Bio Co., Ltd.) was used. According to the manual of the kit, the culturing of osteoclast precursor cells was started in the presence of M-CSF (final concentration: 50 ng/ml) in the A and B groups, and in the presence of M-CSF (final concentration: 50 ng/ml) and MHP1 (final concentration: 30, 50, or 100 µg/ml) in the C and D groups. Thereafter, 24 hours to 7 days after the start of culturing, the A group was cultured in the presence of M-CSF (final concentration: 50 ng/ml), the B group was cultured in the presence of M-CSF (final concentration: 50 ng/ml) and RANKL protein (final concentration: 50 ng/ml), the C group was cultured in the presence of M-CSF (final concentration: 50 ng/ml) and MHP1 (final concentration: 30, 50, or 100 µg/ml), and the D group was cultured in the presence of M-CSF (final concentration: 50 ng/ml), RANKL protein (final concentration: 50 ng/ml), and MHP1 (final concentration: 30, 50, or 100 µg/ml). After culturing, the cells were subjected to TRAP staining and nuclear staining according to a standard method. FIG. 9 shows the results. FIG. 9 (a) shows TRAP staining images of the A, B, and D groups, and FIG. 9 (b) shows TRAP staining images and nuclear staining images of the C group.

FIG. 9 (a) indicated that the differentiation of osteoclasts promoted by RANKL was inhibited by MHP1 (comparison between the B group and the C group). FIG. 9 (b) indicated that the differentiation of osteoclasts did not occur even when MHP1 was added.

Example 7: Stability of RANKL Peptide

The stability of the RANKL peptide was examined. The specific examination procedures were as follows.

Figure 10:
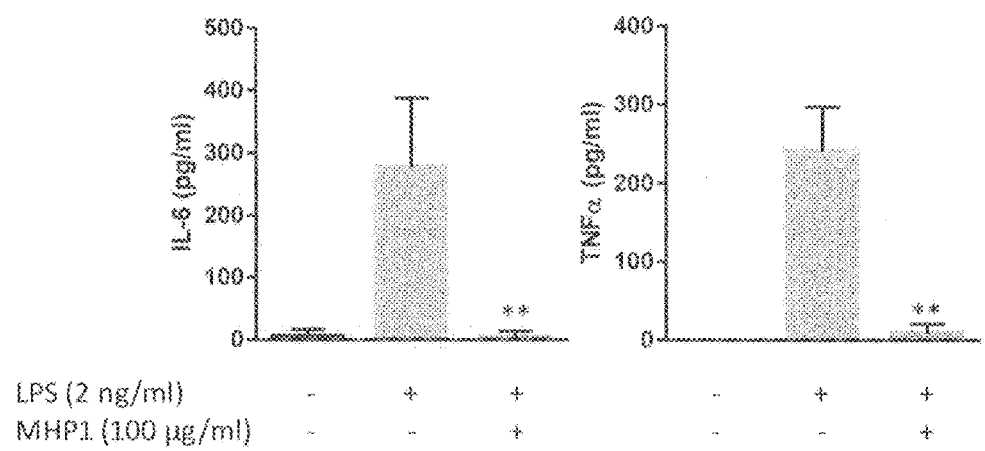
FIG. 10 shows the results of examining the stability of the RANKL peptide (Example 7). The vertical axis represents the concentration of IL-6 or TNF-α in the medium measured by ELISA. "**" indicates that the P-value relative to control was less than 0.01.

MHP1 was dissolved in water to a concentration of 2 mg/ml, and stored at 4° C. for 208 days. Thereafter, MG6 cells (mouse-derived microglial cell line) were cultured in a DMEM medium (+4% FBS) containing MHP1 (final concentration: 100 µg/ml) and LPS (final concentration: 2 ng/ml) for 24 hours by a standard method. After culturing, the concentrations of IL-6 and TNFα in the medium were measured by the ELISA method. FIG. 10 shows the results.

FIG. 10 revealed that MHP1 exhibited a proinflammatory cytokine secretion-inhibiting effect even after long-term storage, in the same manner as MHP1 before storage. This indicated that the stability of MHP1 was high.

Reference Example 2: Synthesis 2 of Oligopeptides

Synthesis of an oligopeptide (MHP1-3) obtained by replacing the methionine residue of MHP1 (Reference Example 1) with the D-isomer thereof, an oligopeptide (MHP1-6) obtained by acetylating the N-terminal of MHP1 (Reference Example 1), an oligopeptide (MHP1-7) obtained by acetylating the N-terminal of MHP1 (Reference Example 1) and amidating the C-terminal of MHP1 (Reference Example 1), and an oligopeptide (MHP1-8) obtained by amidating the C-terminal of MHP1 (Reference Example 1) was entrusted to ILS Inc. It was confirmed by HPLC and MS that oligopeptides with the desired sequences were synthesized with high purity. Hereinafter, these peptides are also referred to as "the RANKL peptide."

Example 8: Analysis 2 of Preventive and Therapeutic Effects on Inflammatory Skin Diseases Whether the RANKL peptide (MHP4) improved psoriatic symptoms caused by the administration of imiquimod (IMQ), which is a psoriatic symptom-inducing agent, was examined. Specifically, the following procedure was performed according to the dosing schedule shown in FIG. 1 except that the first application of an ointment was performed 6 hours after the first imiquimod application. In Example 1, the RANKL peptide aqueous solution was administered, while a RANKL peptide ointment was administered in this example.

As test animals, BALB/c 9-week-old male mice whose back hair was partially removed were prepared. 5% imiquimod (IMQ) was applied to the hair-removed portion in the back and ear of each mouse (62.5 mg per mouse) (day 0 (0 d)). 6 hours later, (1) an MHP4 hydrophilic petrolatum ointment (375 ng (MHP4)/15 mg (hydrophilic petrolatum) per mouse, n=2), hydrophilic petrolatum (control (untreated), n=2), or MCT/BBP (Marduox (tradename) ointment) (15 mg per mouse, n=2) was individually applied to the back and ear. Thereafter, imiquimod and item (1) above were applied every day (from day 1 (1 d)).

Figure 11:
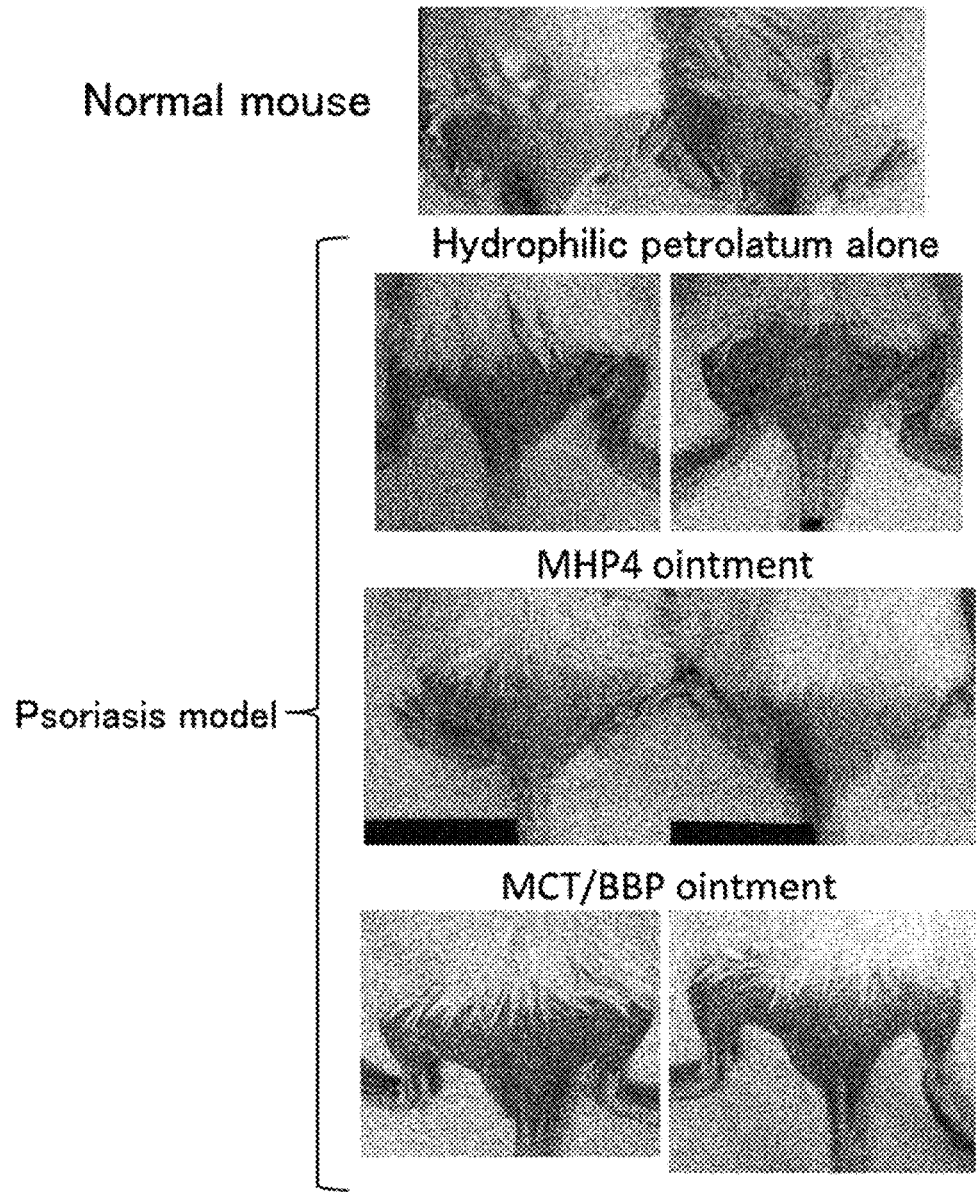
FIG. 11 shows the photographs of backs on day 1 in Analysis 2 of preventive and therapeutic effects on inflammatory skin diseases (Example 8).

FIG. 11 shows the photographs of observation sites in the backs of the mice.

Figure 12:
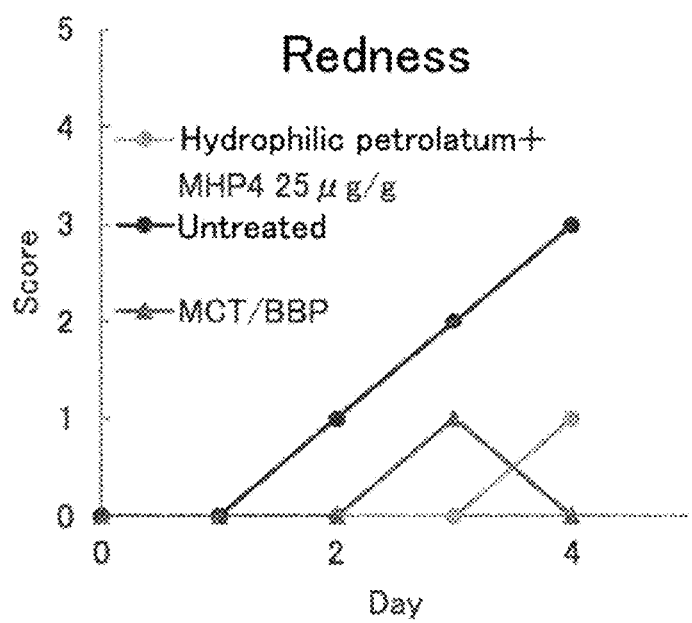
FIG. 12 shows the results of quantifying the degree of redness in Analysis 2 of preventive and therapeutic effects on inflammatory skin diseases (Example 8). The vertical axis represents the numerical value representing the degree of redness (evaluation criteria: none (0), mild (1), moderate (2), severe (3), and very severe (4)), and the horizontal axis represents the number of days elapsed from the first imiquimod administration.
Figure 13:
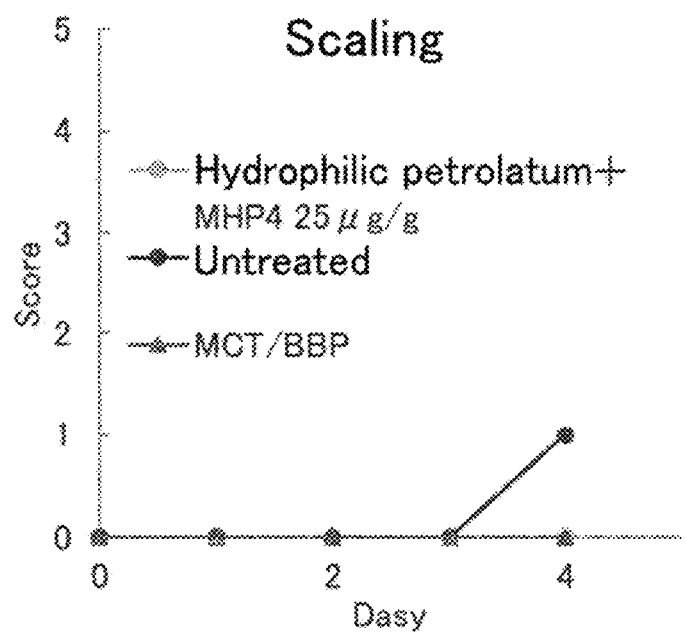
FIG. 13 shows the results of quantifying the degree of white scaling in Analysis 2 of preventive and therapeutic effects on inflammatory skin diseases (Example 8). The vertical axis represents the numerical value representing the degree of white scaling (evaluation criteria: none (0), mild (1), moderate (2), severe (3), and very severe (4)), and the horizontal axis represents the number of days elapsed from the first imiquimod administration.
Figure 14:
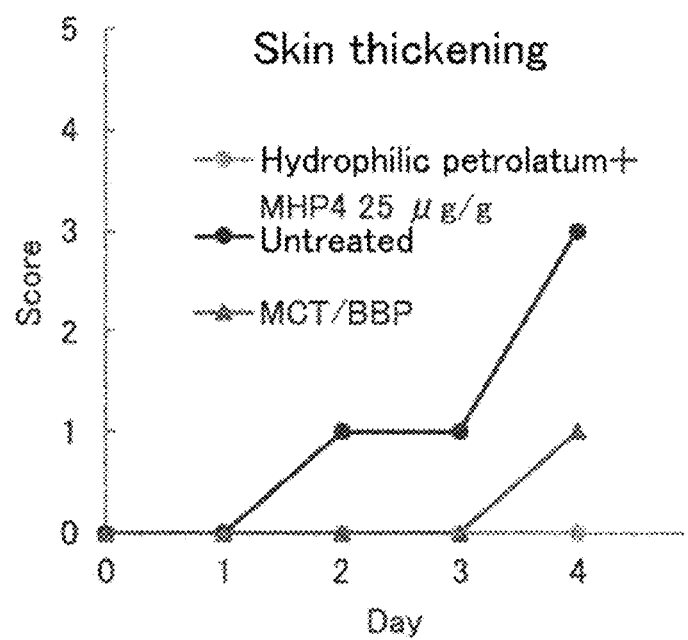
FIG. 14 shows the results of quantifying the degree of skin thickening in Analysis 2 of preventive and therapeutic effects on inflammatory skin diseases (Example 8). The vertical axis represents the numerical value representing the degree of skin thickening (evaluation criteria: none (0), mild (1), moderate (2), severe (3), and very severe (4)), and the horizontal axis represents the number of days elapsed from the first imiquimod administration.

The degree of redness in the back, the degree of white scaling in the back, and the degree of skin thickening in the back were quantified according to the description in the document (van der Fits, L. et al. Imiquimod-induced psoriasis-like skin inflammation in mice is mediated via the IL-23/IL-17 axis. J. Immunol. 182, 5836-45 (2009) (evaluation criteria: none (0), mild (1), moderate (2), severe (3), and very severe (4)). FIGS. 12 to 14 show the results.

FIGS. 11 to 14 indicated that the administration of MHP4 improved psoriasis symptoms.

Example 9: Analysis 3 of Preventive and Therapeutic Effects on Inflammatory Skin Diseases Whether the RANKL peptide (MHP1-8) improved atopic dermatitis symptoms caused by the intradermal administration of a mite antigen, which is an atopic dermatitis-inducing agent, was examined. The specific examination procedures were as follows.

As test animals, BALB/c 6-week-old female mice were prepared. The mite antigen was intradermally administered to the pinna of each mouse (day 0 (0 d)). On day 0 and day 1, (1) an MHP1-8 aqueous solution (50 μg/25 μL per mouse, n=10) or dH$_2$O (control (vehicle), n=10) was applied to each ear.

Figure 15:
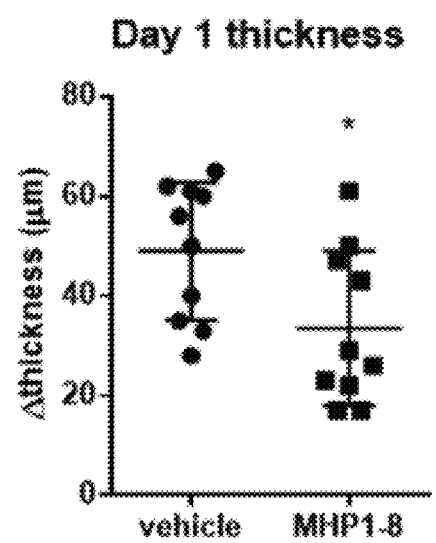
FIG. 15 shows the measurement results of ear thickness in Analysis 3 of preventive and therapeutic effects on inflammatory skin diseases (Example 9). The vertical axis represents the difference between the measured ear thickness and the ear thickness prior to the administration of a mite antigen.

On day 1, the ear thickness was measured. FIG. 15 shows the results.

FIG. 15 indicated that the administration of MHP1-8 improved atopic dermatitis symptoms.

Example 10: Analysis 4 of Preventive and Therapeutic Effects on Inflammatory Skin Diseases Whether the RANKL peptide (MHP1-7) improved psoriatic symptoms caused by the administration of imiquimod (IMQ), which is a psoriatic symptom-inducing agent, was examined. Specifically, the following procedure was performed according to the dosing schedule shown in FIG. 1 except that the first application of an ointment was performed 6 hours after the first imiquimod application. As in Example 8, a RANKL peptide ointment was administered in this example.

As test animals, BALB/c 9-week-old male mice whose back hair was partially removed were prepared. 5% imiquimod (IMQ) was applied to the hair-removed portion in the back and ear of each mouse (62.5 mg per mouse) (day 0 (0 d)). 6 hours later, (1) MHP1-7 hydrophilic petrolatum ointment 1 (3 μg (MHP1-7)/15 mg (hydrophilic petrolatum) per mouse, n=2), MHP1-7 hydrophilic petrolatum ointment 2 (1.5 μg (MHP1-7)/15 mg (hydrophilic petrolatum) per mouse, n=2), or hydrophilic petrolatum (control (untreated), n=2) was individually applied to the back and ear (day 1 (1 d)). Thereafter, imiquimod and item (1) above were applied every day (from day 1 (1 d)).

Figure 16:
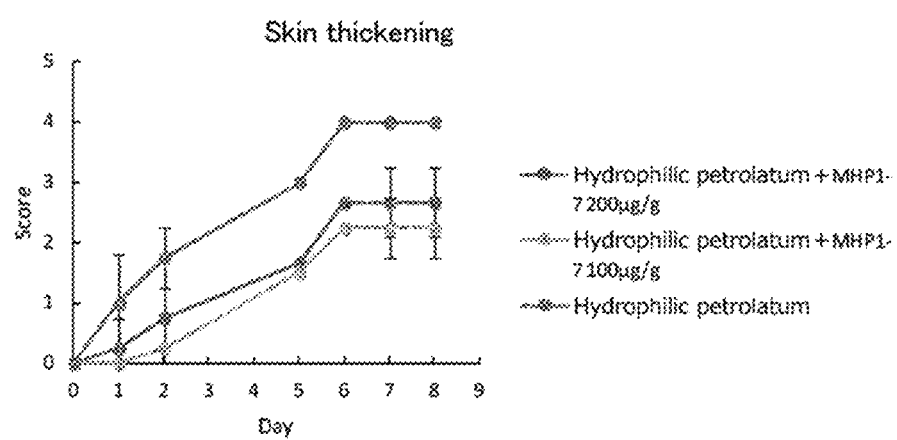
FIG. 16 shows the results of quantifying the degree of skin thickening in Analysis 4 of preventive and therapeutic effects on inflammatory skin diseases (Example 10). The vertical axis represents the numerical value representing the degree of skin thickening (evaluation criteria: none (0), mild (1), moderate (2), severe (3), and very severe (4)), and the horizontal axis represents the number of days elapsed from the first imiquimod administration.

The degree of skin thickening in the back was quantified according to the description in the document (van der Fits, L. et al. Imiquimod-induced psoriasis-like skin inflammation in mice is mediated via the IL-23/IL-17 axis. J. Immunol. 182, 5836-45 (2009) (evaluation criteria: none (0), mild (1), moderate (2), severe (3), and very severe (4)). FIG. 16 shows the results.

FIG. 16 indicated that the administration of MHP1-7 improved psoriasis symptoms.

Example 11: Analysis 5 of Preventive and Therapeutic Effects on Inflammatory Skin Diseases Whether the RANKL peptide (MHP1-7) improved psoriatic symptoms caused by the administration of imiquimod (IMQ), which is a psoriatic symptom-inducing agent, was examined. Specifically, the following procedure was performed according to the dosing schedule shown in FIG. 1 except that the first application of an ointment was performed 6 hours after the first imiquimod application.

As test animals, BALB/c 9-week-old male mice whose back hair was partially removed were prepared. 5% imiquimod (IMQ) was applied to the hair-removed portion in the back and ear of each mouse (62.5 mg per mouse) (day 0 (0 d)). 6 hours later, (1) MHP1-7 hydrophilic cream ointment 1 (1.5 μg (MHP1-7)/15 mg (hydrophilic cream) per mouse, n=4), MHP1-7 hydrophilic cream ointment 2 (1.5 μg (MHP1-7)/15 mg (hydrophilic cream) per mouse, n=4), or hydrophilic cream (control (untreated), n=4) was individually applied to the back and ear (day 1 (1 d)). Thereafter, imiquimod and item (1) above were applied every day (from day 1 (1 d)). Hydrophilic cream ointment 1 was prepared by mixing a MHP1-7 aqueous solution with a hydrophilic cream, and hydrophilic cream ointment 2 was prepared by mixing MHP1-7 in a Transcutol P (diethylene glycol monoethyl ether) solution with a hydrophilic cream.

Figure 17:
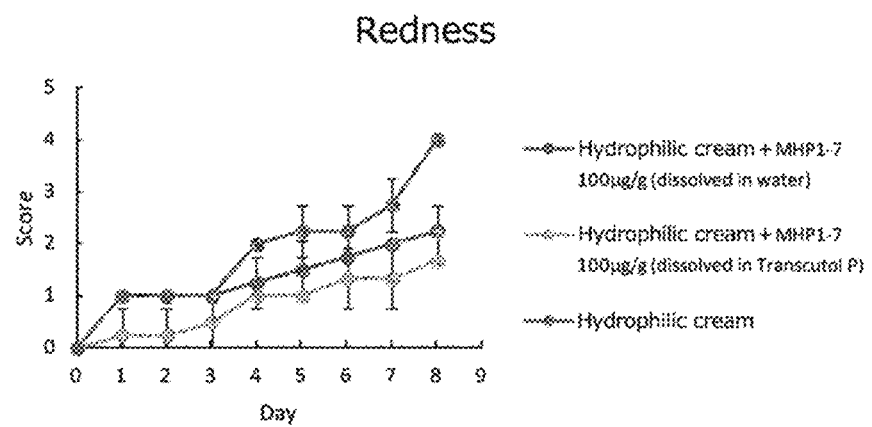
FIG. 17 shows the results of quantifying the degree of redness in Analysis 5 of preventive and therapeutic effects on inflammatory skin diseases (Example 11). The vertical axis represents the numerical value representing the degree of redness (evaluation criteria: none (0), mild (1), moderate (2), severe (3), and very severe (4)), and the horizontal axis represents the number of days elapsed from the first imiquimod administration.
Figure 18:
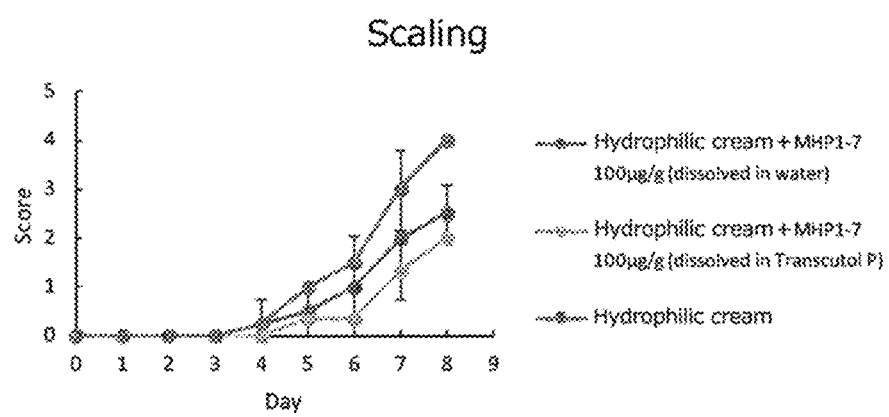
FIG. 18 shows the results of quantifying the degree of white scaling in Analysis 5 of preventive and therapeutic effects on inflammatory skin diseases (Example 11). The vertical axis represents the numerical value representing the degree of white scaling (evaluation criteria: none (0), mild (1), moderate (2), severe (3), and very severe (4)), and the horizontal axis represents the number of days elapsed from the first imiquimod administration.
Figure 19:
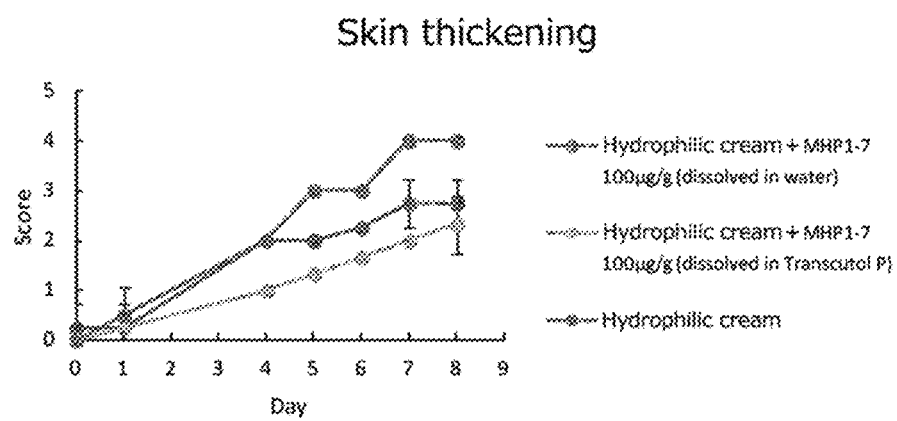
FIG. 19 shows the results of quantifying the degree of skin thickening in Analysis 5 of preventive and therapeutic effects on inflammatory skin diseases (Example 11). The vertical axis represents the numerical value representing the degree of skin thickening (evaluation criteria: none (0), mild (1), moderate (2), severe (3), and very severe (4)), and the horizontal axis represents the number of days elapsed from the first imiquimod administration.

The degree of redness in the back, the degree of white scaling in the back, and the degree of skin thickening in the back were also quantified according to the description in the document (van der Fits, L. et al. Imiquimod-induced psoriasis-like skin inflammation in mice is mediated via the IL-23/IL-17 axis. J. Immunol. 182, 5836-45 (2009) (evaluation criteria: none (0), mild (1), moderate (2), severe (3), and very severe (4)). FIGS. 17 to 19 show the results.

FIGS. 17 to 19 indicated that the administration of MHP1-7 improved psoriasis symptoms. Hydrophilic cream ointment 2 in which a glycol ether solution of RANKL peptide was formed into an ointment had higher improvement effects.

Example 12

RANKL Peptide-Containing Lotion

Each RANKL peptide was dissolved in water to a concentration of 2 mg/ml to produce RANKL peptide-containing lotions.

Example 13

RANKL Peptide-Containing Ointment

The RANKL peptide (MHP4) was mixed with hydrophilic petrolatum to produce an ointment having a concentration of 25 μg/g.

The RANKL peptide (MHP1-7) was mixed with hydrophilic petrolatum to produce ointments having concentrations of 100 μg/g and 200 μg/g.

Example 14

The RANKL peptide (MHP1-7) was mixed with a hydrophilic cream to produce a cream having a concentration of 100 μg/g.

SEQUENCE LISTING

P17-183 WO_PCT_Prevention of Inflammatory Skin Diseases-20171107-104749-1.txt

The invention claimed is:

1. A method for treating an inflammatory skin disease, the method comprising administering to a subject having an inflammatory skin disease an oligopeptide consisting of an amino acid sequence containing a DE loop sequence of RANKL protein and a β-strand D sequence of RANKL protein placed adjacent to the N-terminal side of the DE loop sequence,
   wherein
   the DE loop sequence is the amino acid sequence represented by SEQ ID NO: 1,
   the β-strand D sequence is the amino acid sequence represented by any one of SEQ ID NOs: 2 to 5,
   the amino acid sequence of the oligopeptide is free of a CD loop sequence of RANKL protein,
   the oligopeptide has a length of 50 amino acid residues or less, and
   the inflammatory skin disease is psoriasis.

2. The method according to claim 1, wherein the amino acid sequence of the oligopeptide contains a β-strand E sequence of RANKL protein placed adjacent to the C-terminal side of the DE loop sequence.

3. The method according to claim 2, wherein the β-strand E sequence is the following amino acid sequence (e) or (f):
   (e) the amino acid sequence represented by any one of SEQ ID NOs: 6 to 9, or
   (f) an amino acid sequence with substitution, deletion, addition, or insertion of one to three amino acids in the amino acid sequence represented by any one of SEQ ID NOs: 6 to 9.

4. The method according to claim 1, wherein the amino acid sequence of the oligopeptide is the following amino acid sequence (i) or (j):
   (i) the amino acid sequence represented by any one of SEQ ID NOs: 12, 13, and 15 to 20, or
   (j) an amino acid sequence with substitution, deletion, addition, or insertion of one to three amino acids in the amino acid sequence represented by any one of SEQ ID NOs: 12, 13, and 15 to 20.

5. The method according to claim 1, wherein the amino acid sequence of the oligopeptide is the following amino acid sequence (i') or (j'):
   (i') the amino acid sequence represented by SEQ ID NO: 12, 15, or 16, or
   (j') an amino acid sequence with substitution, deletion, addition, or insertion of one to three amino acids in the amino acid sequence represented by any one of SEQ ID NO: 12, 15, or 16.

6. The method according to claim 1, wherein the oligopeptide has a length of 40 amino acid residues or less.

7. The method according to claim 6, wherein the oligopeptide has a length of 30 amino acid residues or less.

8. A method for inhibiting at least one pathway selected from the group consisting of Toll-like receptor 7 pathway and Toll-like receptor 8 pathway, the method comprising administering an oligopeptide consisting of an amino acid sequence containing a DE loop sequence of RANKL protein and a β-strand D sequence of RANKL protein placed adjacent to the N-terminal side of the DE loop sequence to a subject having inflammatory response elicited through at least one pathway selected from the group consisting of Toll-like receptor 7 pathway and Toll-like receptor 8 pathway,
   wherein
   the DE loop sequence is the amino acid sequence represented by SEQ ID NO: 1,
   the β-strand D sequence is the amino acid sequence represented by any one of SEQ ID NOs: 2 to 5,
   the amino acid sequence of the oligopeptide is free of a CD loop sequence of RANKL protein, and
   the oligopeptide has a length of 50 amino acid residues or less.

9. A method for treating an inflammatory skin disease, the method comprising administering externally to a subject having an inflammatory skin disease a drug that contains an oligopeptide consisting of an amino acid sequence containing a DE loop sequence of RANKL protein and a β-strand D sequence of RANKL protein placed adjacent to the N-terminal side of the DE loop sequence,
   wherein
   the DE loop sequence is the amino acid sequence represented by SEQ ID NO: 1,
   the β-strand D sequence is the amino acid sequence represented by any one of SEQ ID NOs: 2 to 5,
   the amino acid sequence of the oligopeptide is free of a CD loop sequence of RANKL protein,
   the oligopeptide has a length of 50 amino acid residues or less, and
   the inflammatory skin disease is psoriasis.

* * * * *